(12) United States Patent
Rezaie et al.

(10) Patent No.: US 12,390,660 B2
(45) Date of Patent: Aug. 19, 2025

(54) INTERNAL ULTRAVIOLET THERAPY

(71) Applicant: CEDARS-SINAI MEDICAL CENTER, Los Angeles, CA (US)

(72) Inventors: Ali Rezaie, Beverly Hills, CA (US); Mark Pimentel, Los Angeles, CA (US); Gil Y. Melmed, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 18/229,466

(22) Filed: Aug. 2, 2023

(65) Prior Publication Data

US 2024/0024697 A1    Jan. 25, 2024

Related U.S. Application Data

(63) Continuation of application No. 16/300,500, filed as application No. PCT/US2017/035316 on May 31, 2017, now abandoned.
(Continued)

(51) Int. Cl.
*A61N 5/06* (2006.01)
*A61B 1/06* (2006.01)

(52) U.S. Cl.
CPC .............. *A61N 5/0624* (2013.01); *A61B 1/06* (2013.01); *A61B 1/0638* (2013.01);
(Continued)

(58) Field of Classification Search
CPC .... A61N 2005/0603; A61N 2005/0608; A61N 2005/0609; A61N 2005/061;
(Continued)

(56) References Cited

U.S. PATENT DOCUMENTS 5,053,033 A    10/1991    Clarke
5,573,531 A    11/1996    Gregory
(Continued)

FOREIGN PATENT DOCUMENTS

AU    2017273699 A1    12/2018
CA       2515304 A1     2/2004
(Continued)

OTHER PUBLICATIONS

European Search Report for EP21771541.6 dated Apr. 19, 2024, 7 pages.
(Continued)

*Primary Examiner* — Mark W. Bockelman
(74) *Attorney, Agent, or Firm* — Nixon Peabody LLP

(57) ABSTRACT

The disclosed technology relates to a system for delivering UV-A/B light with a catheter to treat infectious or inflammatory disorders in a patient. While UV light in the UV-C range has traditionally been used to treat skin disorders and for focused ablation of plaques in the arteries and other targeted internal uses, it has not been developed for broader infection, inflammation or neoplasia treatment inside the human body. Here, the inventor(s) developed a system for emission of therapeutic doses of UV light via a catheter, capsule, endoscope, tube or port that can be used to manage internal infections and inflammatory conditions inside a patient.

18 Claims, 24 Drawing Sheets

Related U.S. Application Data

(60) Provisional application No. 62/343,710, filed on May 31, 2016.

(52) U.S. Cl.
CPC .............. *A61B 1/0684* (2013.01); *A61N 5/06* (2013.01); *A61N 5/0603* (2013.01); *A61N 2005/0602* (2013.01); *A61N 2005/0608* (2013.01); *A61N 2005/0609* (2013.01); *A61N 2005/061* (2013.01); *A61N 2005/0611* (2013.01); *A61N 2005/0652* (2013.01); *A61N 2005/0661* (2013.01); *A61N 2005/0667* (2013.01)

(58) Field of Classification Search
CPC .... A61N 2005/0611; A61N 2005/0652; A61N 2005/0661; A61N 2005/0667; A61N 5/0603; A61N 5/06; A61N 5/0624; A61B 1/06; A61B 1/0638
See application file for complete search history.

(56) References Cited

U.S. PATENT DOCUMENTS

| | | | |
|---|---|---|---|
| 5,855,203 A | 1/1999 | Matter | |
| 6,316,872 B1 | 11/2001 | Ge et al. | |
| 7,311,722 B2 | 12/2007 | Larsen | |
| 7,409,954 B2 | 8/2008 | Dobkine et al. | |
| 9,023,092 B2 | 5/2015 | Natale et al. | |
| 9,820,798 B2 | 11/2017 | Schwartz | |
| 10,004,918 B2 | 6/2018 | Klang | |
| 10,357,661 B2 | 7/2019 | Hellstrom et al. | |
| 10,842,567 B2 | 11/2020 | Grace et al. | |
| 11,179,575 B2 | 11/2021 | Rezaie et al. | |
| 11,318,325 B2 | 5/2022 | Rezaie et al. | |
| 11,992,699 B2 | 5/2024 | Rezaie et al. | |
| 2002/0120358 A1 | 8/2002 | Lalonde | |
| 2004/0232359 A1 | 11/2004 | Fiset | |
| 2005/0070759 A1* | 3/2005 | Armstrong | A61B 17/0057 600/105 |
| 2005/0075703 A1 | 4/2005 | Larsen | |
| 2005/0106710 A1 | 5/2005 | Friedman et al. | |
| 2005/0107853 A1 | 5/2005 | Krespi et al. | |
| 2005/0177208 A1 | 8/2005 | Irwin | |
| 2006/0047329 A1 | 3/2006 | Krespi et al. | |
| 2006/0069314 A1 | 3/2006 | Farr | |
| 2006/0127531 A1* | 6/2006 | Jobe | A23K 40/20 426/2 |
| 2006/0130846 A1 | 6/2006 | Rife | |
| 2006/0167531 A1 | 7/2006 | Gertner et al. | |
| 2006/0183987 A1 | 8/2006 | Murray | |
| 2006/0217787 A1 | 9/2006 | Olson | |
| 2007/0135874 A1 | 6/2007 | Bala | |
| 2008/0033519 A1 | 2/2008 | Burwell | |
| 2008/0073565 A1 | 3/2008 | Jeon | |
| 2008/0159908 A1 | 7/2008 | Redmond | |
| 2008/0194973 A1 | 8/2008 | Imam | |
| 2008/0257355 A1 | 10/2008 | Rao et al. | |
| 2009/0179547 A1 | 7/2009 | Auday | |
| 2009/0216177 A1 | 8/2009 | Akiyama et al. | |
| 2009/0287137 A1 | 11/2009 | Crowley | |
| 2010/0220472 A1 | 9/2010 | Dahm | |
| 2010/0241198 A1 | 9/2010 | Klepper | |
| 2011/0084275 A1 | 4/2011 | Yamamuro et al. | |
| 2011/0226966 A1 | 9/2011 | Takahashi et al. | |
| 2012/0004710 A1 | 1/2012 | Kerber | |
| 2012/0321509 A1 | 12/2012 | Bak | |
| 2013/0104884 A1 | 5/2013 | Vazales | |
| 2013/0178788 A1* | 7/2013 | Jaquins-Gerstl | A61M 37/00 604/501 |
| 2013/0261368 A1 | 10/2013 | Schwartz | |
| 2013/0274549 A1 | 10/2013 | Natale et al. | |
| 2014/0150782 A1 | 6/2014 | Vazales | |
| 2014/0235942 A1* | 8/2014 | Hellstrom | A61B 1/0615 128/200.26 |
| 2015/0209457 A1 | 7/2015 | Bonutti et al. | |
| 2016/0008624 A1* | 1/2016 | Grossman | A61N 5/0603 607/92 |
| 2016/0038621 A1 | 2/2016 | Victor et al. | |
| 2016/0114185 A1* | 4/2016 | Mankin | A61B 1/07 607/92 |
| 2016/0128767 A1 | 5/2016 | Azamian | |
| 2016/0151639 A1 | 6/2016 | Scharf et al. | |
| 2017/0265942 A1 | 9/2017 | Grace et al. | |
| 2017/0281966 A1 | 10/2017 | Basiony | |
| 2019/0168023 A1 | 6/2019 | Eltorai | |
| 2019/0175938 A1 | 6/2019 | Rezaie et al. | |
| 2020/0046835 A1 | 2/2020 | Kamaev et al. | |
| 2020/0121943 A1 | 4/2020 | Anderson et al. | |
| 2020/0147409 A1* | 5/2020 | Basiony | A61N 5/0601 |
| 2020/0346032 A1 | 11/2020 | Rezaie et al. | |
| 2021/0106844 A1 | 4/2021 | Rezaie et al. | |
| 2022/0040497 A1 | 2/2022 | Rezaie | |
| 2023/0035292 A1 | 2/2023 | Rezaie et al. | |
| 2023/0147752 A1 | 5/2023 | Rezaie et al. | |
| 2023/0302292 A1 | 9/2023 | Rezaie et al. | |
| 2024/0198131 A1 | 6/2024 | Pimentel et al. | |

FOREIGN PATENT DOCUMENTS

| | | |
|---|---|---|
| CA | 3024711 A1 | 12/2017 |
| CN | 1646191 A | 7/2005 |
| CN | 109414591 A | 3/2019 |
| EP | 3463570 A1 | 4/2019 |
| EP | 3893993 | 10/2021 |
| HK | 40001485 A | 2/2020 |
| IN | 201827043869 A | 10/2019 |
| JP | 2000285854 A | 10/2000 |
| JP | 2007-511286 A | 5/2007 |
| JP | 2007511279 A | 5/2007 |
| JP | 2008528188 A | 7/2008 |
| JP | 2009505365 A | 2/2009 |
| JP | 2011530327 A | 12/2011 |
| JP | 2014-233712 A | 12/2014 |
| JP | 2015505678 A | 2/2015 |
| JP | 2019517305 A | 6/2019 |
| KR | 20190015357 A | 2/2019 |
| MX | 2018014694 A | 5/2019 |
| NZ | 748479 A | 10/2021 |
| SG | 11201810515 T | 12/2018 |
| WO | 2010/029292 A1 | 3/2010 |
| WO | 2010058607 A1 | 5/2010 |
| WO | 2011083381 A1 | 7/2011 |
| WO | 2014022867 A1 | 2/2014 |
| WO | 2014165854 A1 | 10/2014 |
| WO | 2017/210366 A1 | 12/2017 |
| WO | 2021076399 A1 | 4/2021 |
| WO | 2021189020 A1 | 9/2021 |
| WO | 2021202402 A1 | 10/2021 |
| WO | 2022036263 A1 | 2/2022 |
| WO | 2022235966 A1 | 11/2022 |

OTHER PUBLICATIONS

International Search Report and Written Opinion for PCT/US2017/035316 dated Oct. 2, 2017, 12 pages.
European Supplementary Search Report for EP17807445.6 dated Feb. 26, 2020, 14 pages.
Extended European Search Report or EP17807445.6 dated Jun. 25, 2020, 13 pages.
ISR and WO for PCT/US20/054758 dated Jan. 11, 2021, 9 pages.
JP Notice of Reasons for Rejection for JP2018-562598 dated Nov, 2, 2020, 16 pages.
NZ Examination Report for App No. 748479 Oct. 14, 2020, 5 pages.
NZ Examination Report for App No. 748479 Mar. 24, 2021, 4 pages.
Hamamoto et al., New water disinfection system using UVA light-emitting diodes, Journal of Applied Microbiology, Aug. 30, 2007, vol. 103:6: 2291-2298.

(56) References Cited

OTHER PUBLICATIONS

Aihara, et al., Vegetable surface Sterilization system using UVA Light-Emitting Diodes, Journal of Medical Investigation, Sep. 27, 2014, vol. 61, pp. 285-290.
SG Written Opinion for 11201810515T dated Mar. 2, 2020, 4 pages.
SG Written Opinion for 11201810515T dated Jan. 20, 2021, 7 pages.
Wikipedia, Inverse-square law, 2021; https://en.wikipedia.org/wiki/inverse-square_law#Light_and_other_electromagnetic_radiation (Year: 2021).
Extended European Search Report for EP 20877251.7 dated Jan. 21, 2022, 6 pages.
ISR-WO for PCT/US2021/023354 dated Jun. 30, 2021, 9 pages.
European Centre for Disease Prevention and Control, Outbreak of severe acute respiratory syndrome coronavirus 2 (SARS-COV-2): increased transmission beyond China—fourth update, Feb. 14, 2020 [retrieved May 26, 2021], retrieved from the internet: <URL: https://www.ecdc.europa.eu/sites/default/files/documents/SARS-CoV-2-risk-assessment-14-feb-2020.pdf>, pp. 1-12.
Pekmezovic et al., Candida pathogens induce protective mitochondria-associated type I interferon signalling and a damage-driven response in vaginal epithelial cells, Nature Microbiology, 2021, pp. 643-657.
ISR-WO for PCT/US2021/046011 dated Nov. 17, 2021, 10 pages.
JP Notice of Reasons for Rejection for JP2018-562598 dated Jul. 7, 2022, 5 pages.
IPRP for PCT/US20/054758 dated Apr. 19, 2022, 9 pages.
EESR for EP 21856823.6 dated Apr. 20, 2024, 8 pages.
IL Office Action for IL 263062, Mar. 26, 2025, 17 pages.
Notice of Reasons for Rejection for JP 2023-509643 dated May 1, 2025, 15 pages.

\* cited by examiner

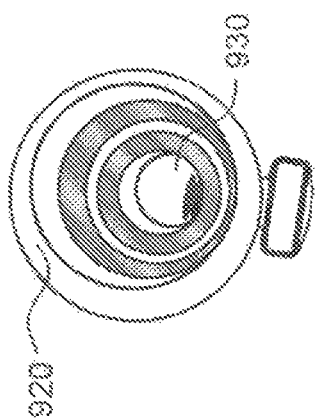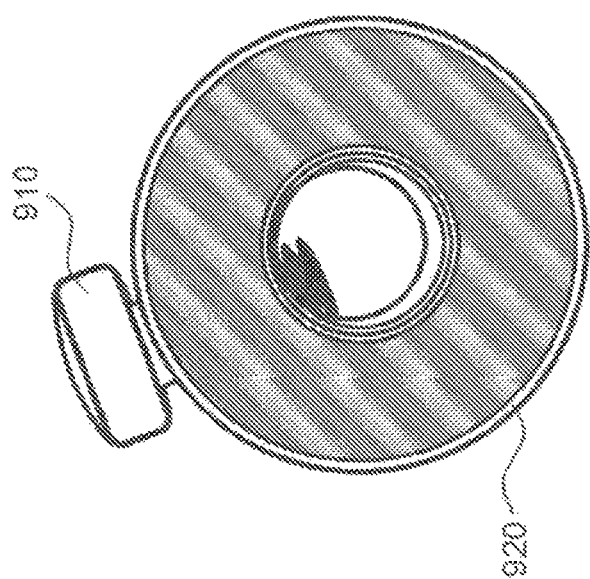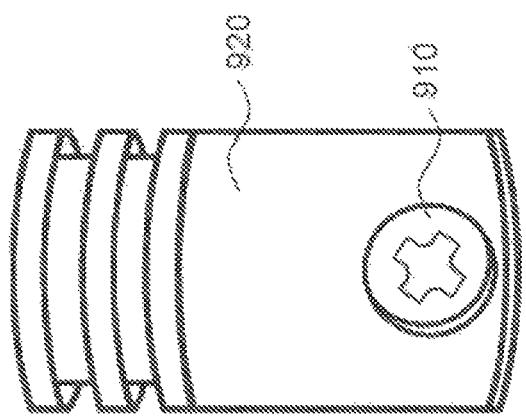

INTERNAL ULTRAVIOLET THERAPY

CROSS-REFERENCE TO RELATED APPLICATIONS

This application claims the benefit under 35 U.S.C. § 120 as a continuation of U.S. patent application Ser. No. 16/300,500, filed Nov. 9, 2018, which is the National Phase of International Application No. PCT/US2017/035316, filed May 31, 2017, which designated the U.S. and that International Application was published under PCT Article 21 (2) in English, which also includes a claim of priority under 35 U.S.C. § 119 (e) to U.S. provisional patent application No. 62/343,710, filed May 31, 2016, the entirety of which is hereby incorporated by reference.

FIELD OF THE DISCLOSURE

The present invention is directed to a device, a method, and a system for ultraviolet therapy. More particularly, the present disclosure relates to a device, a method, and a system for intra-corporeal ultraviolet therapy.

BACKGROUND OF THE DISCLOSURE

The following description includes information that may be useful in understanding the present invention. It is not an admission that any of the information provided herein is prior art or relevant to the presently claimed invention, or that any publication specifically or implicitly referenced is prior art.

Twenty-first century is considered the era of superbugs. More and more resistant strains of bacteria, fungi and viruses are being detected. Current research in development of antibiotics has lagged behind the adaptation capabilities of microorganisms that continue to mutate and cause a rise in infectious diseases. A safe alternative to antibiotics can prove to be extremely valuable and can potentially save millions of lives per year.

In addition to infectious diseases, immune-mediated and inflammatory diseases continue to pose a global challenge. Despite significant strides that have been made in past several decades, treatment of these diseases remain suboptimal. For example, many of patients with inflammatory bowel disease (Crohn's disease and ulcerative colitis), continue to suffer with inadequate subjective and objective control of their disease despite treatments which are extremely expensive and have significant side effects. An intrusive surgical intervention remains the only viable option when medical therapy fails. A safe and effective low-cost alternative to such therapies would save billions of dollars in health care cost and improve the quality of life for millions of patients. Moreover, given the direct interplay of microbiome and inflammation, a treatment options which can target both entities simultaneously is of utmost importance.

SUMMARY OF THE DISCLOSURE

Ultraviolet light is invisible and non-ionizing segment of light spectrum that is divided into three spectrums: (1) UV-A (320 to 400 nm), (2) UV-B (280 to 320 nm), and (3) UV-C (110 to 280 nm). All these components are present in sunlight but UV-C is almost fully absorbed by ozone layer and does not reach the earth surface. UV-A and UV-B are involved in the formation of Vitamin D in human skin. Although UV-C light is traditionally used for disinfection of non-organic surfaces (e.g. hospital rooms, aquariums, air vents, and the like), UV-A and UV-B light have significant anti-inflammatory and antibiotic effects as well. The antibiotic effects of UV-A and UV-B light is induced via damage to haploid DNA/RNA of microorganisms such as bacteria, archaea, fungi, yeast and viruses within minutes. UV light is even capable of stopping the disease process in prion-related diseases that currently has no cure.

However, mammalian diploid DNA is significantly more resistant to such damage. For example, it takes decades of direct sun exposure for select individuals with relevant gene susceptibility and skin type to develop precancerous skin lesions. UV phototherapy is widely being used in management of skin diseases, such as, for example, psoriasis, vitiligo, atopic dermatitis, eczema, Kaposi sarcoma, lichen planus, skin lymphoma, neonatal jaundice, and the like. Such process has been proposed and used as adenomatous polyp detection tool on colonoscopy and also has been proposed in conjunction with a super glue for closing patent foramen ovale.

Considering the anti-inflammatory and antibiotic effects of UV-A and UV-B light, it has the potential to revolutionize the management of non-dermatologic (i.e., internal organs) infections and inflammatory diseases. While UV light has traditionally been used to treat skin disorders, it has not yet been developed for broader infection or inflammation treatment in vivo.

Accordingly, a system has been developed as described herein for emission of therapeutic doses of UV light using vehicles, such as, for example, a catheter, capsule, endoscope, tube or port, for treating or managing internal infections and/or inflammatory conditions inside a patient. For instance, in some examples, the inventors developed devices that can deliver therapeutic doses of UV light in the UV-A/B range from a catheter, endoscope, capsule, or other device to treat infections and inflammatory conditions inside the patient.

In another instance, a system utilizing LEDs or a cold cathode emission that can emit light to cover a broad area inside the body has been developed. Accordingly, these systems may emit UV-A and/or UV-B light emitted from a catheter, endoscope, or other device inside the body to treat or manage infections or inflammatory conditions.

EMBODIMENTS

Embodiment 1. A system for performing intra-corporeal ultraviolet therapy, the system including: a delivery tube, wherein the delivery tube includes an electrical connecting means; at least one UV light source inside the delivery tube that is configured to emit wavelengths, wherein the at least one UV light source is positioned to deliver radiation directed outwardly around the circumference of the delivery tube for a substantial length of the delivery tube; and a power supply connected to the UV light source via the electrical connecting means inside the delivery tube.

Embodiment 2. The system of Embodiment 1, wherein the delivery tube is at least partially transparent.

Embodiment 3. The system of Embodiment 1, wherein the light source is a string of LEDs.

Embodiment 4. The system of Embodiment 1, wherein the light source is a cold cathode tube.

Embodiment 5. The system of Embodiment 1, wherein the light source is a neon filled tube.

Embodiment 6. The system of Embodiment 1, wherein the delivery tube is an endoscope.

Embodiment 7. The system of Embodiment 1, wherein the delivery tube is a catheter.

Embodiment 8. The system of Embodiment 1, wherein the wavelengths include at least one of UV-A, UV-B, or any combination thereof.

Embodiment 9. A system for performing intra-corporeal ultraviolet therapy, the system including:
  a delivery tube, wherein the delivery tube includes an electrical connecting means;
  a UV light source inside the delivery tube positioned to emit UV wavelengths outward from the tube and around the circumference of the tube; and
  a power supply connected to the UV light source by the electrical connection means inside the delivery tube.

Embodiment 10. The system of Embodiment 9, wherein the delivery tube is a catheter that includes a lumen that is configured to pass over a guide wire.

Embodiment 11. A capsule for performing intra-corporeal ultraviolet therapy, the capsule including:
  a battery;
  a UV light source connected to the battery inside the capsule positioned to emit UV wavelengths outward from the capsule and in all directions outside of the capsule; and
  a biocompatible and non-biodegradable casing covering the battery and UV light source.

Embodiment 12. The capsule of Embodiment 11, wherein the UV light source is configured to radiate UV-A and UV-B radiation and filter UV-C radiation.

Embodiment 13. The capsule of Embodiment 11, wherein the UV light source is at least one LED.

Embodiment 14. The capsule of Embodiment 11, wherein capsule is a suppository.

Embodiment 15. The capsule of Embodiment 11, wherein the casing is configured for swallowing.

Embodiment 16. A system for performing intra-corporeal ultraviolet therapy, the system including:
  a delivery rod, wherein the delivery rod includes a borosilicate segment and a silica segment;
  a UV light source, wherein the UV light source is configured to emit wavelengths including at least one of: UV-A and UV-B; and
  a light source attachment, wherein the light source attachment is configured to be placed between the delivery rod and the UV light source.

Embodiment 17. The system of Embodiment 16, wherein the system further includes a power source that is connected to the UV light source.

Embodiment 18. The system of Embodiment 17, wherein the light source attachment includes:
  a body, wherein the body includes a front-end aperture that is configured to connect to the light source, and a back-end aperture, wherein the back-end aperture is configured to connect to a rod; and
  a fastening mechanism, wherein the fastening mechanism includes at least one of: a screw, flat-ended stopper screw, and a nail,
  wherein the fastening mechanism is configured to connect the body to the rod and stabilize position of the rod in relation to the light source.

Embodiment 19. The system of Embodiment 18, wherein the light source attachment further includes a convex lens that is configured to be placed between the front-end aperture and the back-end aperture in order to decrease light loss from the UV light source.

Embodiment 20. The system of Embodiment 17, wherein the silica segment is pure silica.

Embodiment 21. The system of Embodiment 17, wherein the silica segment is abraded on its surface along its length.

Embodiment 22. The system of Embodiment 17, wherein the borosilicate segment is closer to the UV light source than the silica segment.

Embodiment 23. A method of treating a patient for an inflammatory or infectious condition inside the patient's body, the method including:
  providing the UV treatment system of claim 1, claim 8, and claim 17;
  inserting the delivery tube inside a patient cavity; and
  turning on the power supply to emit an amount of UV-A and/or UV-B radiation effective for treatment of the infectious or inflammatory condition.

Embodiment 24. A system for performing intra-corporeal ultraviolet therapy, the system including:
  a delivery rod including a UV-C filtering segment and a UV transmission segment; and
  at least one UV light source directed towards the filtering segment;

Embodiment 24. The system of Embodiment 24, wherein the filtering segment includes borosilicate.

Embodiment 25. The system of Embodiment 24, wherein the delivery rod is flexible.

Embodiment 26. The system of Embodiment 24, wherein the delivery rod is configured to transmit UV-A and UV-B light.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 9A illustrates a side view of an example of a light source attachment that is constructed in accordance with the principles of the present disclosure;

FIG. 9B illustrates a bottom view of an example of a light source attachment that is constructed in accordance with the principles of the present disclosure;

FIG. 9C illustrates a top view of an example of a light source attachment that is constructed in accordance with the principles of the present disclosure;

Figure 1:
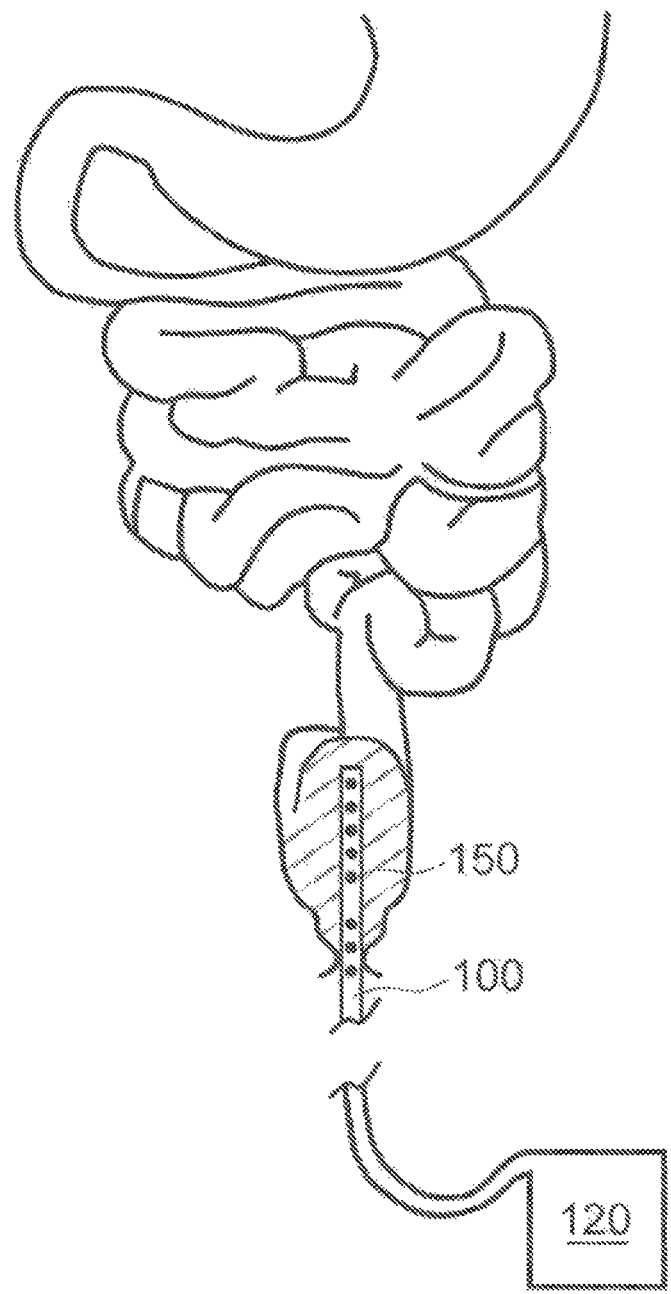
FIG. 1 illustrates a cross sectional view of UV emitting device inserted into the rectum of a patient that is constructed in accordance with the principles of the present disclosure.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described. For example, the Figures primarily illustrate the present invention in the gastrointestinal tract, but as indicated throughout, the disclosed systems and methods can be used for other applications.

In some embodiments, properties such as dimensions, shapes, relative positions, and so forth, used to describe and claim certain embodiments of the invention are to be understood as being modified by the term "about."

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Overview

While UV light in the UV-A and UV-B range has traditionally been used to treat dermatologic disorders and for focused ablation of plaques in the arteries and other targeted internal uses, it has not been developed for broader infection or inflammation treatment inside the human body. The present disclosure describes a system for emission of therapeutic doses of UV light via a catheter, capsule, endoscope, tube, or port that can be used to manage internal infections and inflammatory conditions inside a patient. Delivery of the UV light can be with or without a concomitant photosensitizer.

FIG. 1 illustrates an example of a UV light administrative system that includes a delivery tube 100 and several UV light sources 150, and a power source 120 to power the system. Accordingly, as illustrated, a caregiver (e.g., physician) has navigated the delivery tube 100 to the colon and turned on the power source 120 to emit therapeutic light (e.g., UV light) into the colon region.

FIGS. 9A-9E illustrates an example of a UV light administrative system that includes a light source attachment 900, wherein the light source attachment 900 is configured to be attached between the UV light source 950 and the delivery rod 940.

Delivery Vehicles

Various delivery tubes 100 or other delivery vehicles may be utilized to delivery therapeutic UV light to various portions of the inside of the body. For instance, the delivery tube 100 may be a suitable catheter, endoscope, capsule (for swallowing or suppository), or other device capable of housing one or more UV light sources 150.

In an embodiment of the present disclosure, the UV delivery tube 100 may include various scopes such as endoscopes that may be inserted rectally or orally and navigated to the appropriate regions to deliver effective amounts of anti-inflammatory or other therapeutic doses of UV light. In another embodiment of the present disclosure, the UV delivery tube 100 may include a catheter that is suitable for insertion into the arteries, urethra, vagina and urinary tract, ear canal, etc. In yet another embodiment of the present disclosure, the UV delivery tube 100 may include an indwelling urinary catheter that can be inserted into a patient's bladder. Similarly UV light can be emitted via a light source inside an inflatable balloon catheter to internal organs such as, e.g., vagina, rectum, gastroesophageal junction, stomach, biliary tract, or the like. In yet another embodiment of the present disclosure, the UV light can be emitted via a light source inside a glove or cot that can be worn by a patient or a doctor. The UV light can be inserted digitally and into a patient's orifice, e.g., a mouth, a rectum, a vagina, and the like.

The delivery tube 100 may be configured to include features that accommodate the light sources 150 that are placed inside the tube 100. For instance, the LED light sources 150 may be placed inside a hollow canal inside the tube 100 and wired together in the middle. In other examples, the delivery tube 100 may include a hollow canal for a guide wire to be inserted through and the light sources 150 and associated wiring may instead be embedded in the shell.

In another embodiment of the present disclosure, the light sources 150 may be distributed along the entire portion of the delivery tube 100, an end portion of the delivery tube 100 or other suitable layouts so a broader application of the light sources 150 can be achieved.

Figure 10:
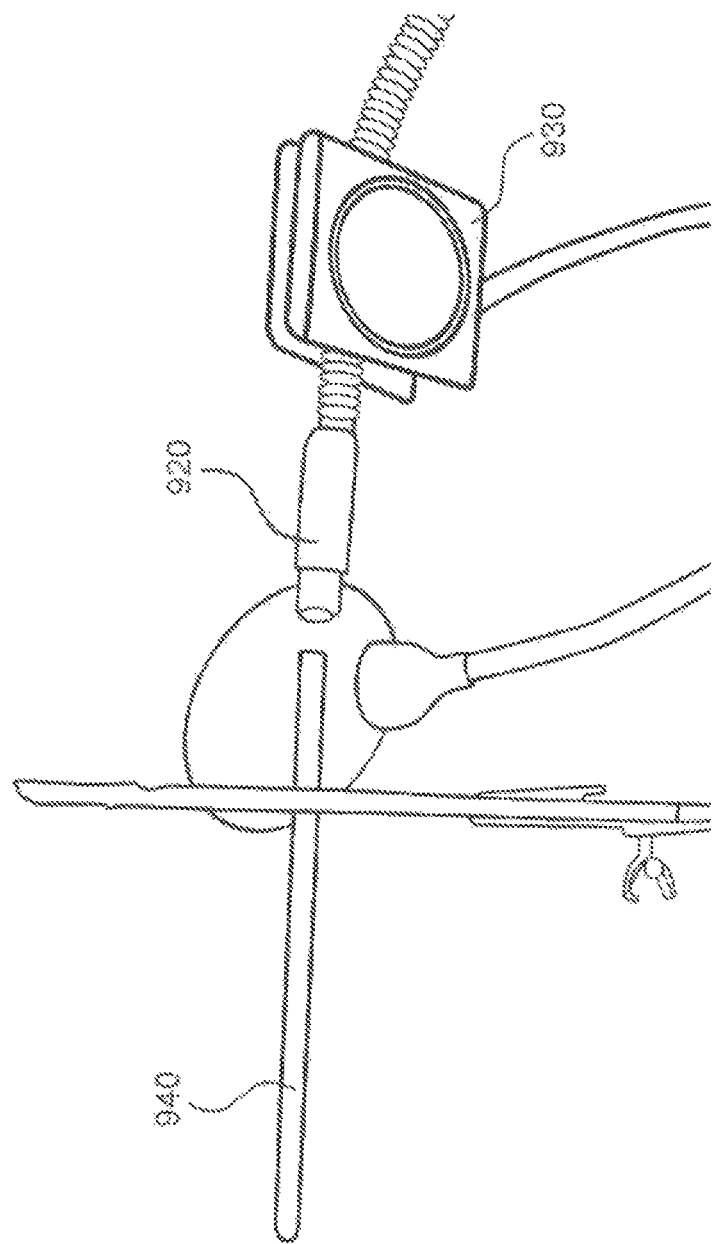
FIG. 10 illustrates an example of a UV emitting device that is constructed in accordance with the principles of the present disclosure.

In yet another embodiment of the present disclosure, the delivery tube (or rod) 100 may be constructed in a way that the entire delivery tube glow and transmit UV light homogenously throughout the entirety of the delivery tube as shown in, e.g., FIG. 10. The delivery tube 100 may be configured to conduct lights in UV-A and/or UV-B ranges only, and not in UV-C range. Furthermore, the delivery tube 100 may be configured to limit thermoconduction to 10 mm. In another embodiment of the present disclosure, the delivery tube may be configured to carry out thermoconduction beyond 10 mm. The light may be incorporated in continuous and pulse therapy depending on efficacy and treatment variables as determined by a physician.

The delivery tube (or rod) 100 may be made of any suitable construction (e.g., rigid or flexible), including various polymers that are biocompatible or have a biocompatible coating. In an embodiment of the present disclosure, the delivery tube 100 may include at least an outer layer of transparent material to allow the UV light from the light sources 150 to radiate out to the internal cavities. In an embodiment of the present disclosure, the delivery tube 100 may be made from, e.g., silicon, silica, borosilicate, polyurethane, polyethylene, Teflon/PTFE, borosilicate, or other suitable materials.

In another embodiment of the present disclosure, the delivery vehicle may include a capsule instead of a delivery tube 100. In such scenario, the capsule may be inserted orally or anally and the capsule may emit light for a certain period of time. For instance, a capsule may include a clear or semi-transparent polymer or other biocompatible coating that may be smooth to allow for passage of the capsule. In some examples, the capsule may include the light source 150 and a power supple 120 such as a small battery. The capsule may be deployed and pinned to an internal organ for prolonged light exposure.

For instance, the capsule a smooth coating, internal batteries that power UV lights 150 such as LEDs that are positioned to emit light in all direction from the capsule. Accordingly, as the capsule passes through the digestive system it may deliver the therapeutic light until it is excreted.

Light Sources

Figure 2:
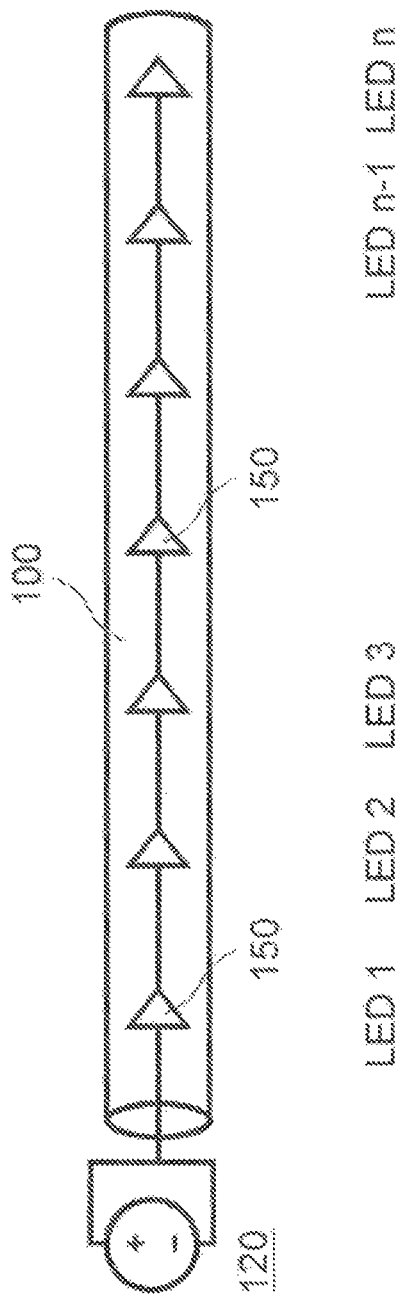
FIG. 2 illustrates a schematic view of UV emitting device that incorporate LEDs that is constructed in accordance with the principles of the present disclosure.

Depending on the delivery tube 100 or other delivery device, various light sources 150 may be utilized that are capable of emitting UV light. For instance, FIG. 2 illustrates an embodiments of a flexible delivery tube 100 (e.g., catheter, endoscope, or the like) that includes a string of LED light sources 150 that are distributed along the tube 100. Each of the light sources 150 are attached together with electrical connections and connected to a power supply 120. The light sources 150 may be advantageous, since their small size and low power requirements enable them to be placed along the delivery tube 100.

Accordingly, if the light sources 150 are placed along the delivery tube 100, the light sources 150 may deliver a UV light to a large delivery area inside the patient. Accordingly, the therapeutic target area may be relatively lame, to treat inflammatory diseases that may affect a large portion of the colon.

Figure 3:
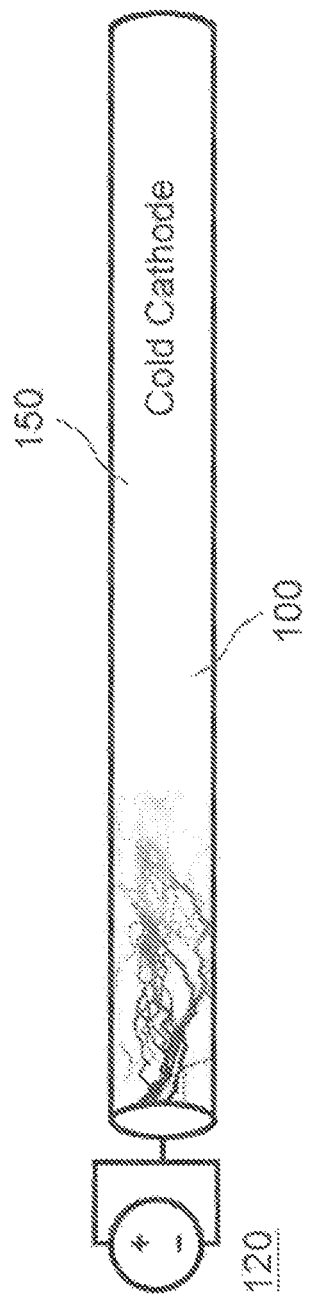
FIG. 3 illustrates a schematic view of UV emitting device that incorporates a cold cathode that is constructed in accordance with the principles of the present disclosure.

FIG. 3 illustrates an example of where a delivery tube 100 includes a light source 150 that is a cold cathode powered by a power supply 120. In this embodiment, the cold cathode light source 150 delivers light through a transparent, flexible delivery tube 100. This embodiment may include an inert gas that fills the delivery tube (or a vacuum tube) 100. The delivery tube 100 may include, e.g., a cold cathode tube. The delivery tube 100 may include any cathode light emitter that is not electrically heated by a filament. For instance, a cold cathode fluorescent lamp may utilize a discharge in mercury vapor to emit ultra violet light.

However, in most embodiments, the gases utilized in the tube should be inert for safety. For instance, neon gas vapor may be energized with a 12 volt power supply 120 to generate sufficient UV light. In other examples, other power supplies with various voltages and/or currents will be utilized to develop sufficiently intense light at the current wavelength.

In some embodiments, the light sources 150 may emit x-rays. For these embodiments, the system may include vacuum tubes or x-ray tubes.

The power supply 120 may include an on/off switch or other controls to turn on and off the light sources 150. In some examples, the power supply will include the ability to turn on the UV light source at various intensities, or to modulate the intensity over time depending on the therapeutic application. The power supply may be different for different types of UV light sources 150. For instance, the power requirements for an LED implementation may be less than for a cold cathode implementation.

In another embodiment of the present disclosure and as shown in, e.g., FIGS. 9A-9E, a UV light administrative system may include a delivery rod 900, UV light source 950, and a light source attachment 920, wherein the light source attachment 920 is configured to be attached between the UV light source 950 and the delivery rod 900. The delivery rod 900 may include a borosilicate segment 950 which omits UVC from the light spectrum followed by a segment made out of pure silica (quartz) 900 to extent transmission distance of UV A/B with minimal loss. For example, using only a pure quartz segment has shown to result in detection of significant UV-C light emission (e.g., 4,300 microWatt/cm$^2$ UV-C), whereas using pure quartz rod with a short segment of borosilicate in between the UV light source 950 and the delivery rod 900 (e.g., borosilicate filter) results in above level of detection of UV-A and UV-B (e.g., over 30 cm) and only 10 microwatt/cm$^2$ of UV-C light at the tip of the delivery rod 900, which means that the UV light is reflected back to the body of the delivery rod 900 for a uniform delivery of the UV light throughout the delivery rod 900. The UV light source 950 may be configured to be connected to a power source (not shown) that powers the UV light source 950.

Referring to FIGS. 9A-E and 10 concurrently, the delivery rod 940 may be made by scoring using industrial diamond, whereby the glass cutter oil is used and bilateral pressure to snap clearly (rather than opaque) is applied. The tip of the delivery rod 940 may be rounded by a drill (e.g., 500 RPM drill) wherein the drill uses a premium diamond polish pad (e.g., 120-200 grit premium diamond polish pad) and sandpaper (e.g., 400 sandpaper). Afterwards, a body of the delivery rod 900 may be sanded with a 120-200 grit premium diamond polish pad so that the UV-C free light (e.g., UV-A and UV-B) can emit throughout the body of the delivery rod 900.

Light Source Attachment

Referring to FIGS. 1, 9A-9E, and 10, each of the UV light administrative device may include a light source attachment 900 that is placed between a delivery rod 940 (or delivery tube 100) and a light source 950 (or a power source 120). The light source attachment 900 may include a body 920 and a fastening mechanism 910 (e.g., a screw, a stopper screw, a fastener, a nail, and the like) that attaches the body 920 to an enclosure (e.g., a rod, a catheter, a handle, or the like). The body 920 may include a front-end aperture 970 that is configured to connect to a light source (or power supply) and a back-end aperture 980 that is configured to connect to a rod (or catheter). A diameter of the front-end aperture 970 may be around 10.1 mm and a diameter of the hack-end aperture 980 may be around 5 mm. The fastening mechanism 910 may be around 3 mm in length. The light source attachment 900 may be made of aluminum for heat conduction and for decreasing light intensity deterioration. The diameter of both the front-end aperture 970 and the back-end aperture 980 may vary in order to fit, e.g., a particular catheter, tube, rod, or the like. The light source attachment 900 may also include a convex lens 930 between the front-end aperture 970 and the back-end aperture 980 that is configured to decrease the light loss. The convex lens may include semi-convex heat resistant lens that decreases light loss and focuses the light.

UV Ranges

Figure 4:
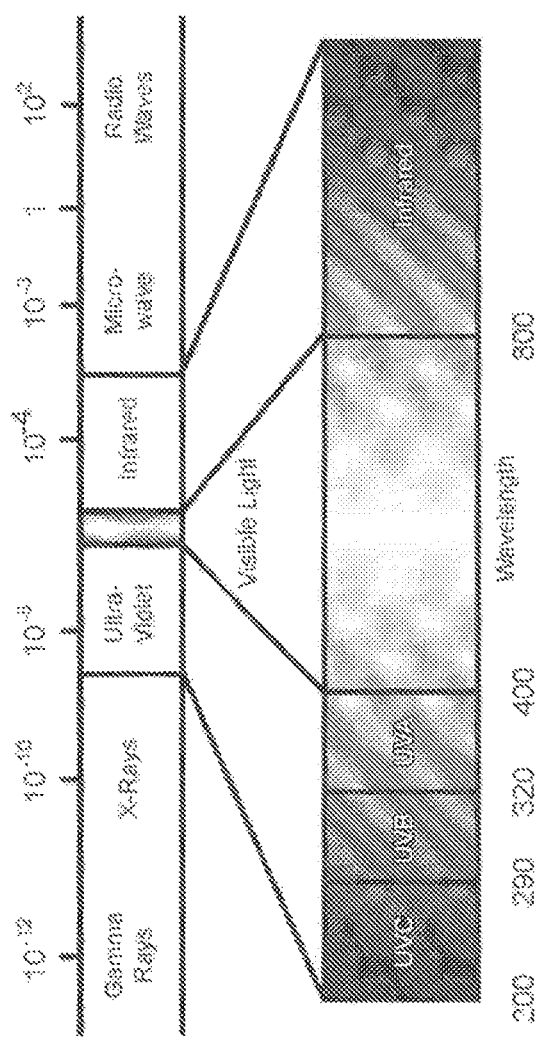
FIG. 4 illustrates an example of a schematic of the UV spectrum.

FIG. 4 illustrates UV ranges that may be implemented by the disclosed devices and methods. For instance, the light sources may deliver light only the UV-A and UV-B ranges, and not in the UV-C ranges. In other examples, the systems and methods may deliver light in all three UV ranges, or also deliver light in the visible spectrum. In some examples, only UV-A light or only UV-B light may be emitted for certain indications and treatments.

Other Electromagnetic Ranges

In some examples, for the treatment of end stage intestinal GVHD or neoplasia, the ranges that may be emitted also includes x-ray wavelengths. X-ray wavelengths have wavelengths that are just shorter than UV-C range light.

EXAMPLES

The following examples are provided to better illustrate the claimed invention and are not intended to be interpreted as limiting the scope of the invention. To the extent that specific materials or steps are mentioned, it is merely for purposes of illustration and is not intended to limit the invention. One skilled in the art may develop equivalent means or reactants without the exercise of inventive capacity and without departing from the scope of the invention.

GI Tract Treatments

Figure 5:
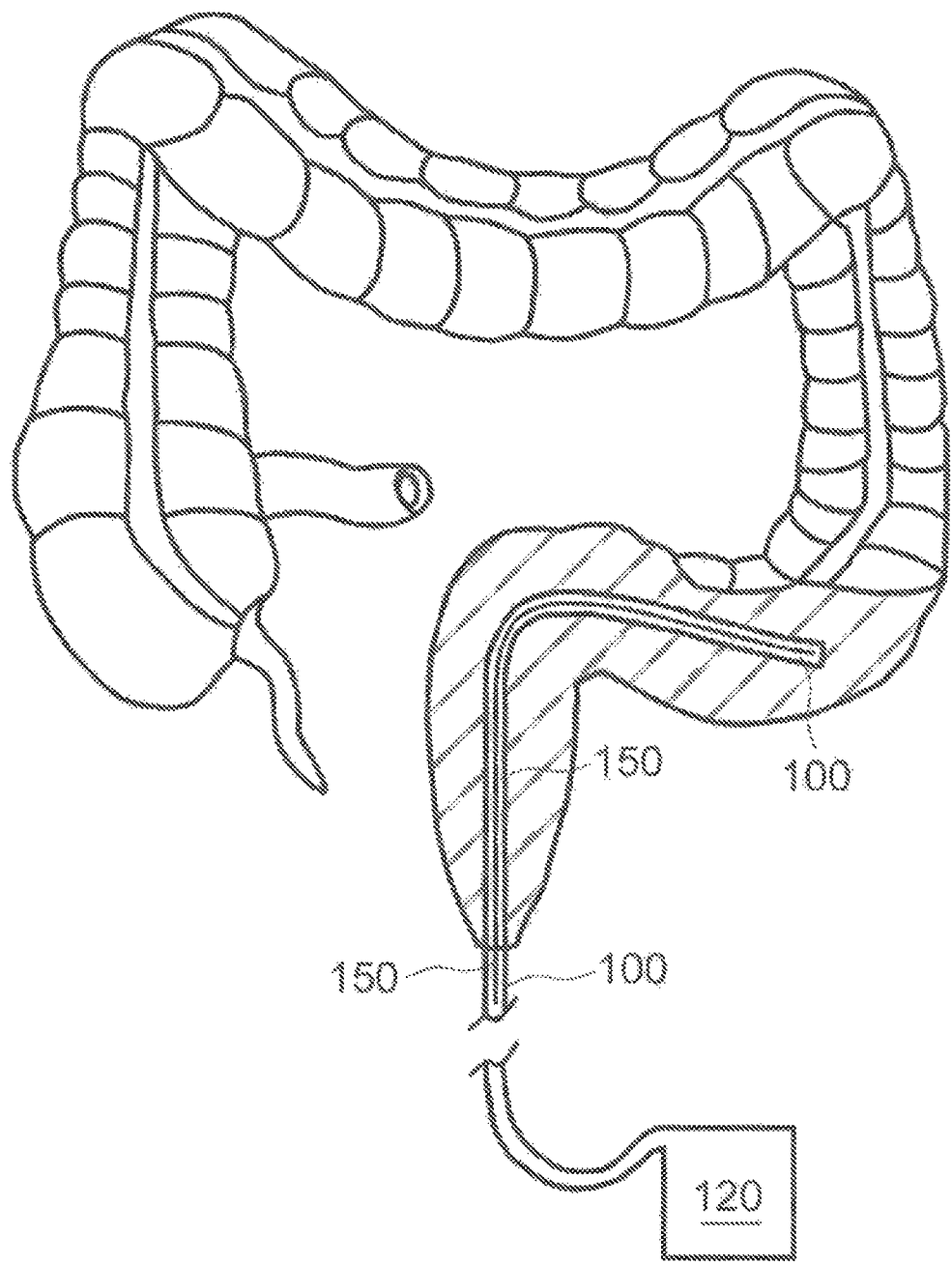
FIG. 5 illustrates a cross sectional view of UV emitting device inserted into the rectum of a patient that is constructed in accordance with the principles of the present disclosure.
Figure 6:
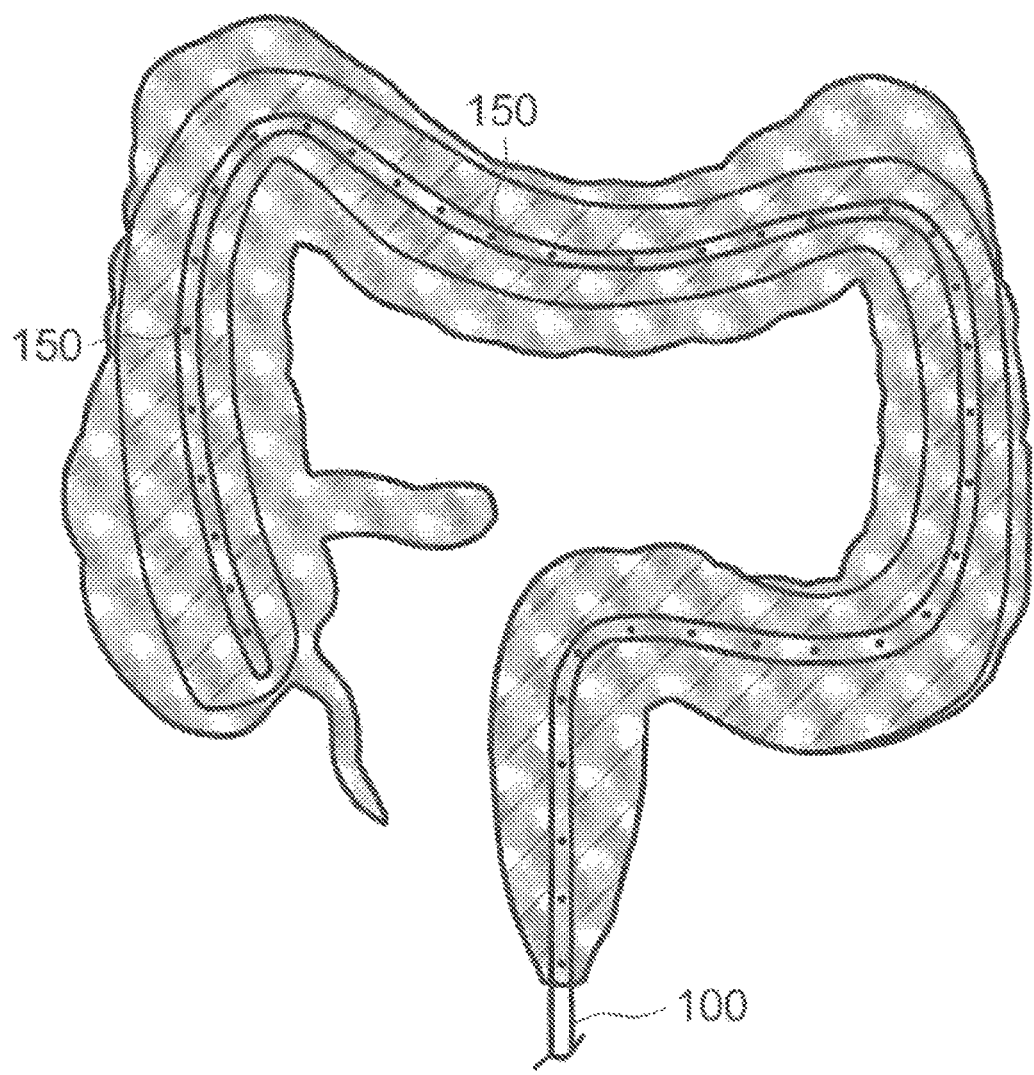
FIG. 6 illustrates a cross sectional view of UV emitting device inserted into the colon of a patient that is constructed in accordance with the principles of the present disclosure.

FIGS. 5-6 illustrate example applications to treat disorders in the colon and/or rectum. For instance, FIG. 5 illustrates a delivery tube 100 that includes light sources 150 may be inserted by the caregiver into the colon through the anus. Then, the delivery tube 100 may be navigated to the therapeutic site for instance the colon, a portion or most of the intestines (see, e.g., FIG. 6), or the stomach via mouth (see, e.g., FIG. 7). Then, the power supply (or light source) 120 may be turned on to illuminate the therapeutic site with UV light 150.

In some examples, this may be utilized to treat various inflammatory diseases including ulcerative and Crohn's colitis, IBD, infectious diseases and others as more fully described herein. As illustrated, depending on the size, location and type of disease, the delivery tube 100 may include varying amounts of light sources 150 that may be embedded or contained in certain portions or lengths of the delivery tub 100.

Figure 7:
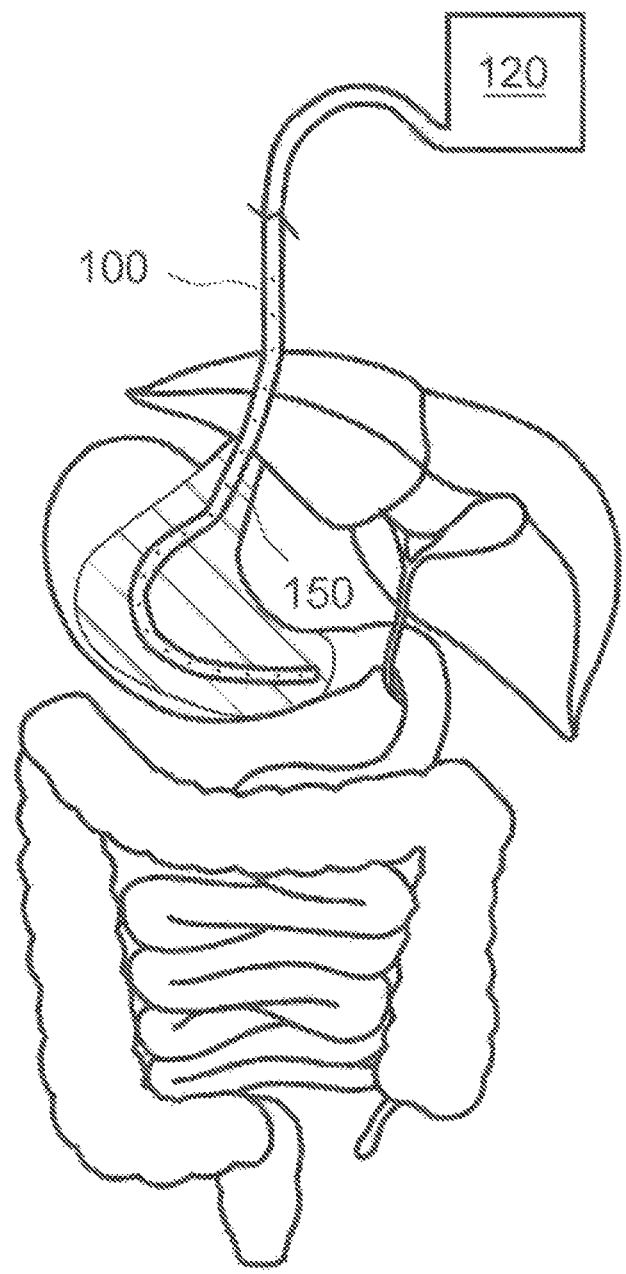
FIG. 7 illustrates a cross sectional view of UV emitting device inserted in the esophagus and stomach of a patient that is constructed in accordance with the principles of the present disclosure.

FIG. 7 illustrates an embodiment where an endoscope or other delivery tube 100 is inserted through the oral cavity through the esophagus into the stomach. In this example, an infection or inflammatory disease in the stomach may be treated with the UV light sources 150.

Capsule

Figure 8:
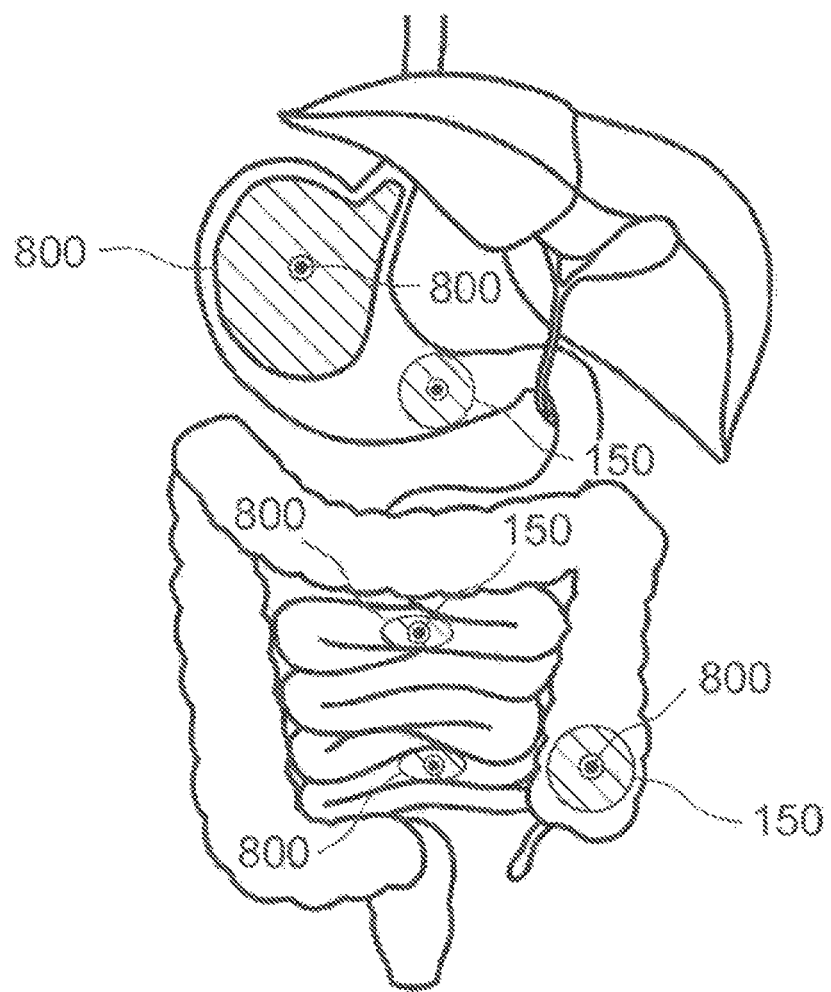
FIG. 8 illustrates a cross sectional view of UV emitting devices swallowed and traveling through the digestive system of a patient that is constructed in accordance with the principles of the present disclosure.
Figure 9D:
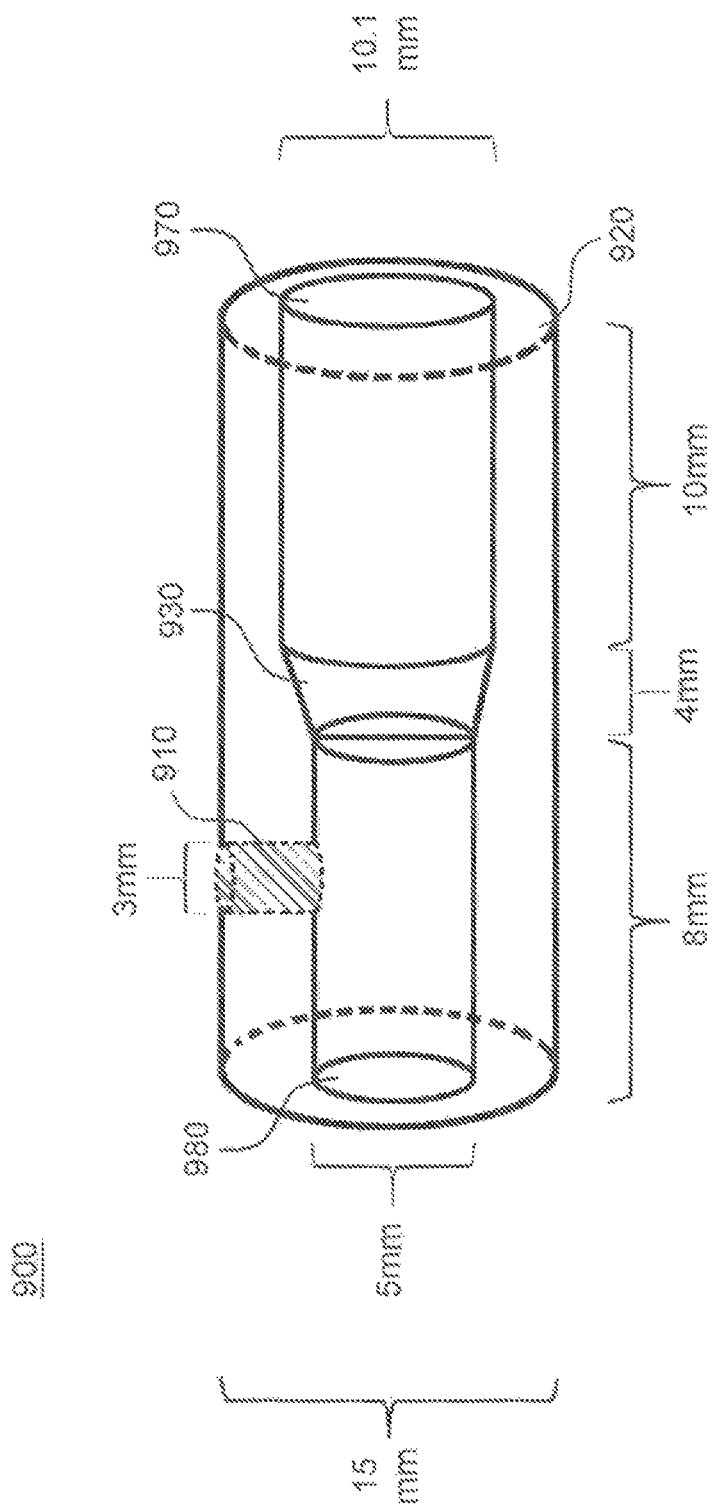
FIG. 9D illustrates a side view of an example of a light source attachment that is constructed in accordance with the principles of the present disclosure.
Figure 9E:
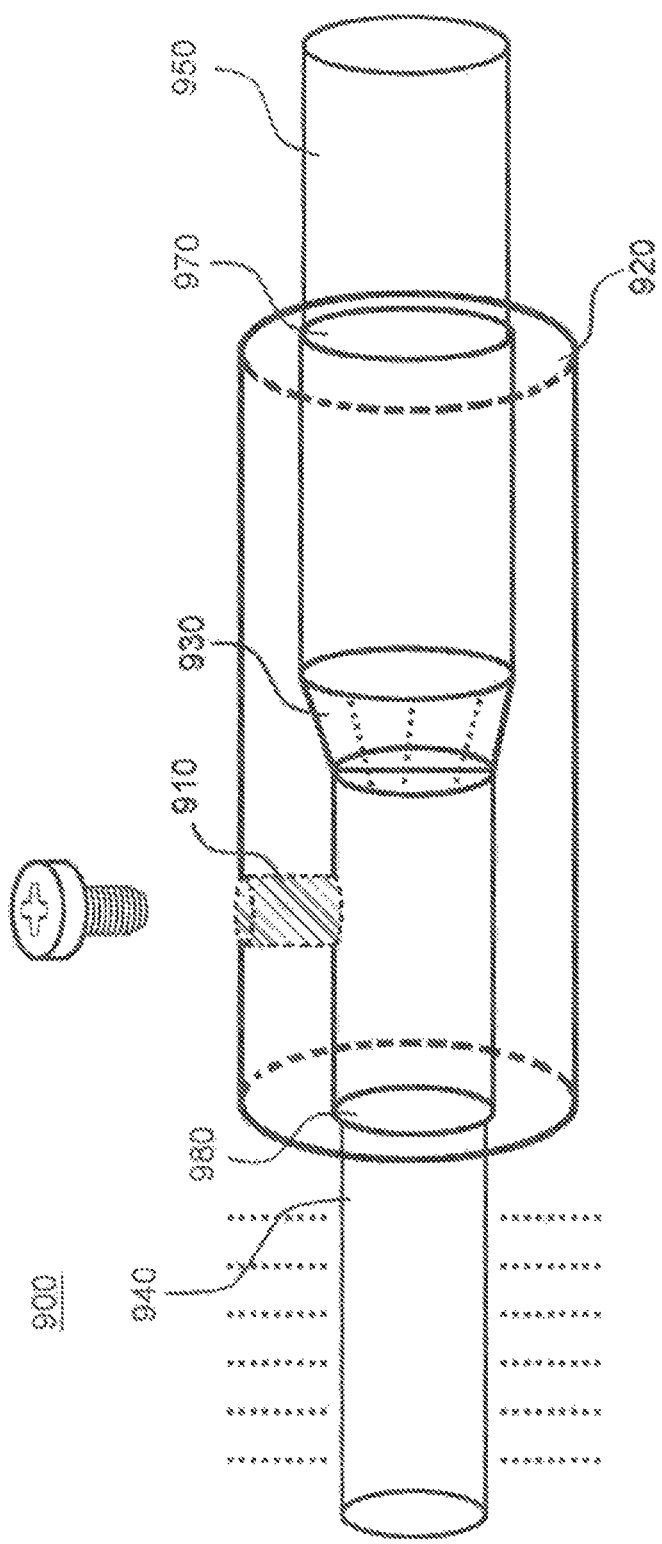
FIG. 9E illustrates a side view of an example of a light source attachment being uses in accordance with the principles of the present disclosure.

FIG. 8 illustrates an example of a system that utilized a capsule 800 tier delivery device that may be swallowed by the patient. The capsule 800 may contain a light source 150 and a power supply 120 for powering the light source 150. In some examples the capsule will be made, or portions of it will be made of transparent material to allow the light to radiate through the capsule. Capsule may contain a tracking device to assess the location of the capsule inside the gastrointestinal tract. Capsule delivery system may be clipped in a hollow organ for continuous or intermittent controlled delivery.

In some examples, the capsule may be the size of a pill or smaller, and may be orally ingestible. The capsule may include a tinier for turning on and off the UV light source when the capsule reaches or is most likely to reach a certain portion of the digestive tract. For instance, the capsule may contain a simple timer to turn on the capsule after 30 minutes, an hour or two hours. For example, the capsule may not turn on the light source 150 until the capsule has reached the digestive tract to treat MS or other infectious or inflammatory conditions.

Catheter

In some examples, the delivery device may be a catheter tube 100 that may be insertable into the arteries, urethra or other parts of a patient's body. For instance, the catheter tube 100 may include a hollow portion that allows for a guide wire to pass through. Accordingly, a caregiver may navigate a guide wire to the treatment site and then pass the catheter over the guide wire to navigate the catheter to or beyond the treatment site.

The catheter tube 100, like the endoscope implementation, may then contain any variety of light sources 150 suitable for administering UV treatment to the inside of an artery. In some examples, this implementation may use smaller light sources 150 such as LEDs.

Figure 11:
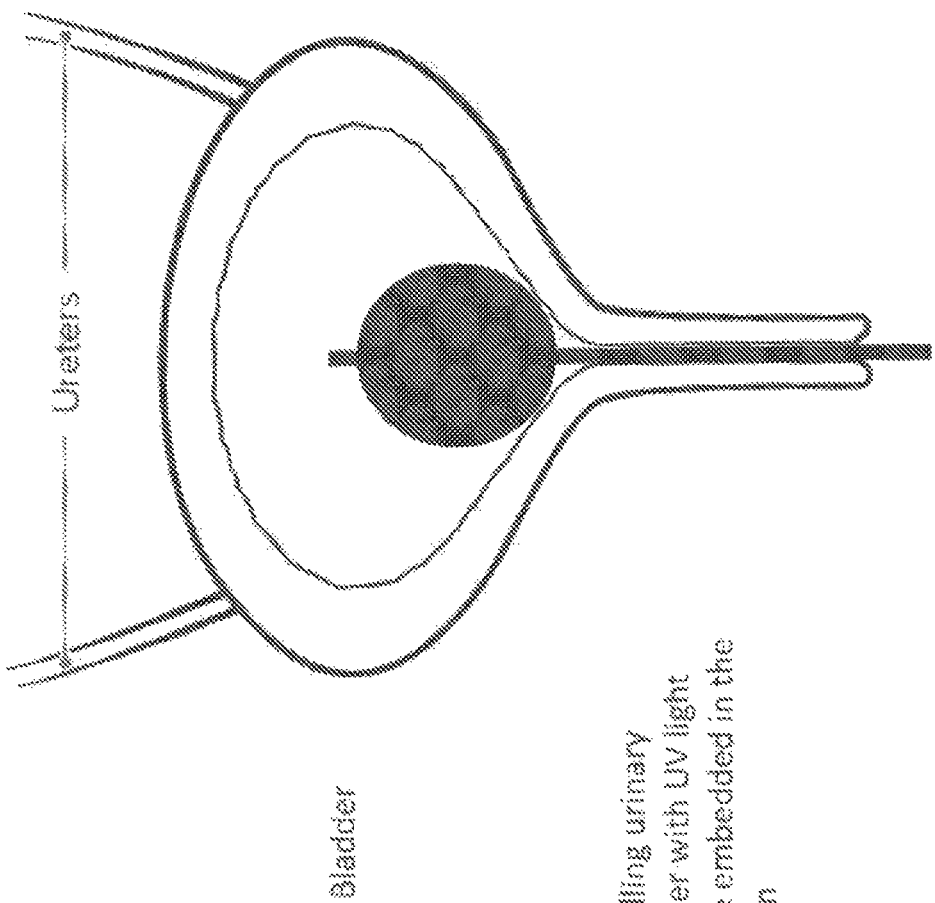
FIG. 11 illustrates an example of method for using the UV emitting device on foley catheter in accordance with the principles of the present disclosure.

In another example of the present disclosure, the delivery device may be a catheter tube 100 that may be inserted into a bladder as an indwelling urinary catheter (as shown in, e.g., FIG. 11), so that it disinfects the urinary tract infection with UV lights. In another example, the delivery device may be a part of a balloon inserted into a rectum to treat the rectum with UV lights. In yet another example, the delivery device may be incorporated into a vaginal rod to treat infection in a patient's vagina.

Extracorporeal

In other examples, the blood from the patient (e.g., with a dialysis machine) may be routed extracorporeal and the blood radiated with UV light (e.g., UV-A and UV-B). In these examples, the blood may be passed through a machine that radiates the blood with UV light before routing the blood back to the patient. In this example, a much stronger or higher powered UV-A and UV-B light may be utilized because there would be less risk to the bodily tissues other than the cells inside the blood.

Treatment Regimens

The procedures herein may be utilized to treat a number of different inflammatory and infectious diseases. Accordingly, different amounts or time period dosages of UV radiation may be administered depending on the following: (1) type of disease, (2) type of light source. (3) light source power, (4) light source UV range, and (5) severity of the infection or inflammation. For instance, in some embodiments, the time of administration will be determined by the capsule digestion rate, and other factors (e.g., light source power, UV range, and the like) can be manipulated to vary the dosage. In other examples, the endoscope may be delivered by the physician/surgeon for an hour, 30 minutes, two hours, or other suitable times.

Following are examples of treatment regimens and their applications. Accordingly, the devices and methods disclosed herein may be adapted to treat these different conditions.

GI Tract
1. Treatment of ulcerative colitis and Crohn's disease and acute/chronic pouchitis and other chronic inflammatory bowel diseases (IBD)
2. Treatment of non-IBD related proctitis
3. Treatment of IBD or non-IBD related fistula
4. Treatment of inflammatory strictures
5. Treatment of microscopic colitis
6. Treating infectious diarrhea using UV light emitting capsules
7. Treating refractory *Helicobacter pylori* and MALT lymphoma
8. Treatment of esophageal lichen planus and pemphigus vulgaris
9. Treatment of refractory *Clostridium difficile*
10. Treatment of colonic inertia, tropical sprue, celiac disease, small intestinal bacterial overgrowth, typhlitis post-bone marrow transplant infections, pseudopolyps (similar to nasal polyps) and radiation enteritis
11. Treatment of Barrett's esophagus with or without dysplasia
12. Treatment of hepatic encephalopathy with daily UV light capsule
13. Treatment of blind loop syndrome in Roux en Y patients by placing an ILT (Internal light therapy) catheter through a PEG in the remnant stomach
14. Treating perianal fistulas with transparent setons which can emit UV light
15. Decreasing the rate of infection associated with percutaneous feeding or suction tubes
16. Treatment of gastrointestinal cancers limited to mucosa and submucosa
17. Treatment of hepatobiliary infections, inflammation and cancers limited to mucosa and submucosa Urology and Nephrology
1. Sterilizing blood in patients with known bacteremia, fungemia, or viremia during dialysis to eradicated or to decrease the microorganism load. Alternative a light needle can be placed in fistula to be turned on even outside of dialysis window. Ex vivo sensitivity analysis will be done fir narrower wavelength but more intense ILT.
2. Sterilizing indwelling urinary catheters in catheter dependent patients
3. Treatment of bladder and urethral cancer limited to mucosa and submucosa
4. Treatment of refractory cystitis/urinary tract infection
5. Adding UV phototherapy to peritoneal dialysis catheter to decrease the risk of peritonitis and even long term peritoneal sclerosis.

Cardiology
1. Sterilizing blood in patients with known bacteremia, fungemia or viremia with LVAD to eradicated or to decrease the microorganism load. Alternative a light needle can be placed in fistula to be turned on even outside of dialysis window. Ex vivo sensitivity analysis can be done for narrower wavelength but more intense UV therapy.
2. Refractory bacterial and fungal endocarditis being treated with direct UV light exposure of valves. A photosensitizes may be given intravenously in this case.

Dentistry
1. Treatment of gingivitis.
2. Treatment leukoplakia and oral lichen planus.
3. Treatment of cancers limited to mucosa and submucosa.

Respirology
1. Placing an ILT tube while suctioning ET tube to eliminate the bacteria in the tube and also the bacteria accumulating around the larynx to prevent pneumonia.

2. Build ET tube with ILT capability with intermittent emission.
3. Improving the treatment of empyema by equipping chest tubes with ILT.

Hematology/Oncology
1. Treatment of intestinal Graft-versus-host disease. Xray wavelength will be emitted in this case, leading to death of lymphocytes. This can be used in patients with endstage Crohn's disease awaiting small bowel transplant or palliative care.

ENT
1. Treatment of chronic sinusitis.
2. Treatment of chronic otitis.
3. Treatment of acute otitis media in patients requiring tympanostomy.
4. Treatment of nasal polyps (there is evidence that UV light shrinks them, see attached paper).
5. Treatment of halitosis.
6. Treatment of recurrent tonsillitis/pharyngitis.
7. Treatment of cancers limited to mucosa and submucosa Surgery
1. Improving the treatment of abscesses by equipping the drains with UV light technology.
2. use with surgical drains to avoid superimposed infection.
3. Accelerating anastomosis healing process.
4. Aid in preventing adhesions.

Neurosurgery
1. Intrathecal fibro-optic delivery of UV light in treatment of refractory meningitis.
2. Treatment of refractory shunt infections.
3. Treatment of prion diseases with intrathecal or subarachnoid UV therapy. 4—Treating JC virus related Progressive multifocal leukoencephalopathy by decreasing viral load.

Gynecology
1. Treatment of bacterial or fungal vaginosis.
2. Treatment of rectovaginal/colovesical fistula.
3. Treatment of cancers limited to mucosa and submucosa Rheumatology
1. Intraarticular ILT for treatment of inflammatory and infectious large joint arthritis.

Figure 14:
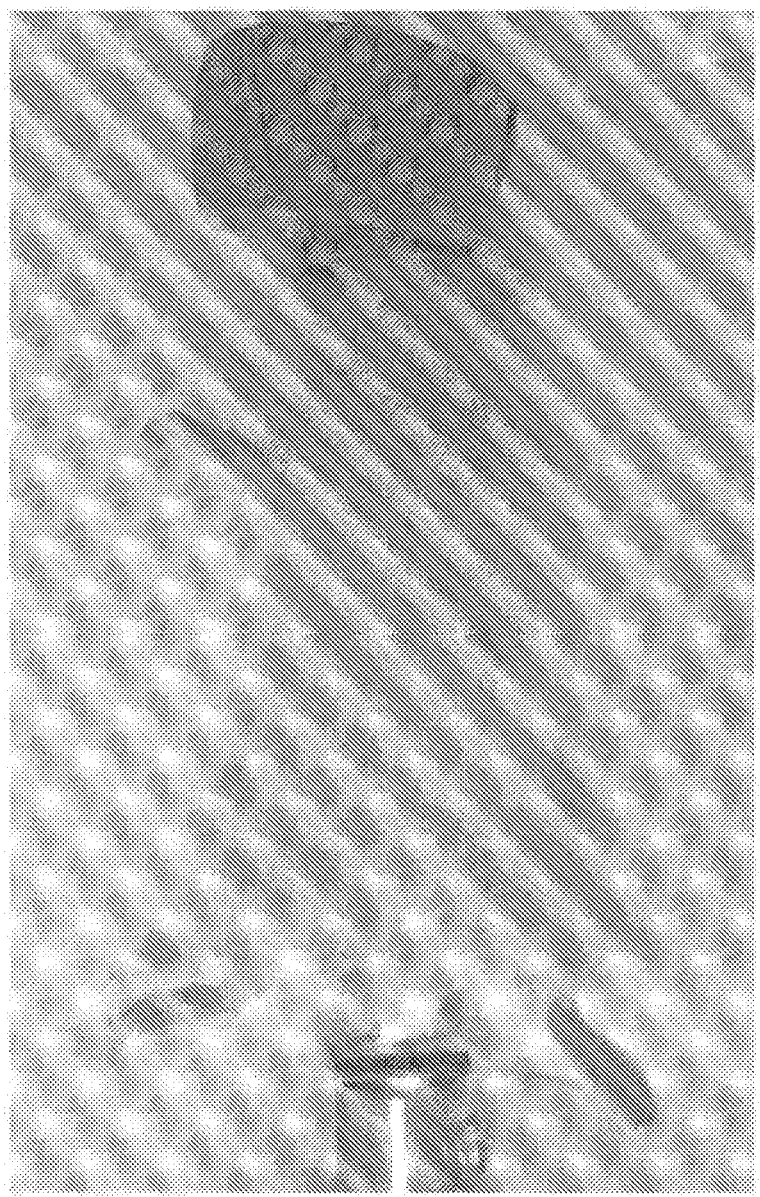
FIG. 14 illustrates an example of a UV emitting device of the present disclosure being used on a colonoscopy on a mouse.

Colonoscopy
1. FIG. 14 illustrates an example of a UV emitting device being used on a colonoscopy on a mouse. The colonoscopy has been carried out safely. The parameters have included a normal colonoscopy 72 hours after 10 minutes and 30 minutes of UV exposure with 1,100 microWatt/cm$^2$ intensity.

Figure 15B:
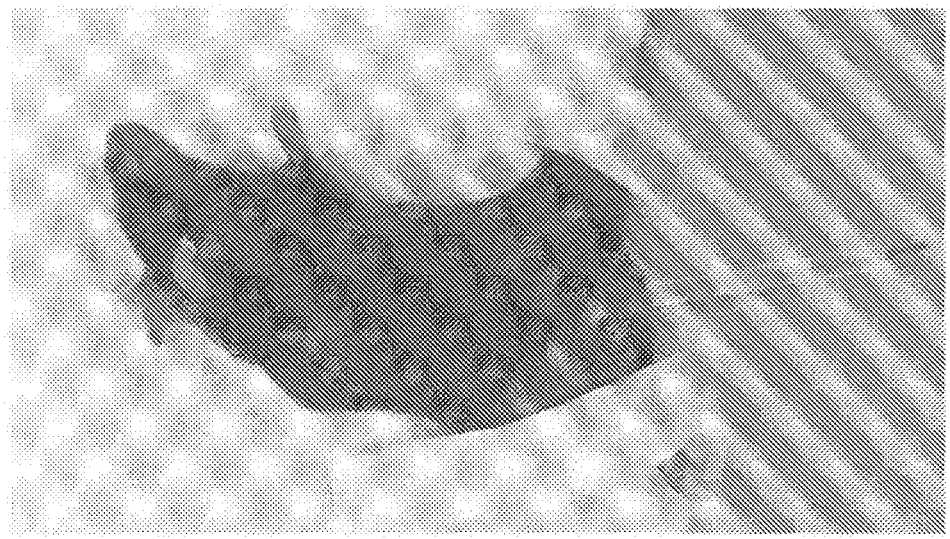
FIGS. 15A and 15B illustrate an example of a UV emitting device of the present disclosure being used on a vaginal treatment on a mouse.
Figure 15A:
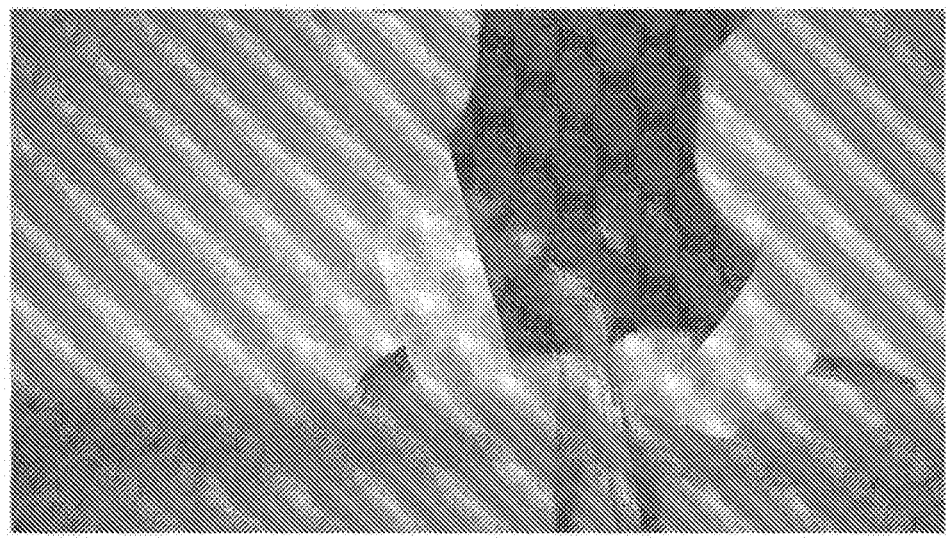

Vaginal Therapy
1. FIGS. 15A and 15B illustrate an example of a UV emitting device being used on a vaginal treatment of a mouse.

EXPERIMENTS

The following set of experimental data is provided to better illustrate the claimed invention and is not intended to be interpreted as limiting the scope.

Figure 12:
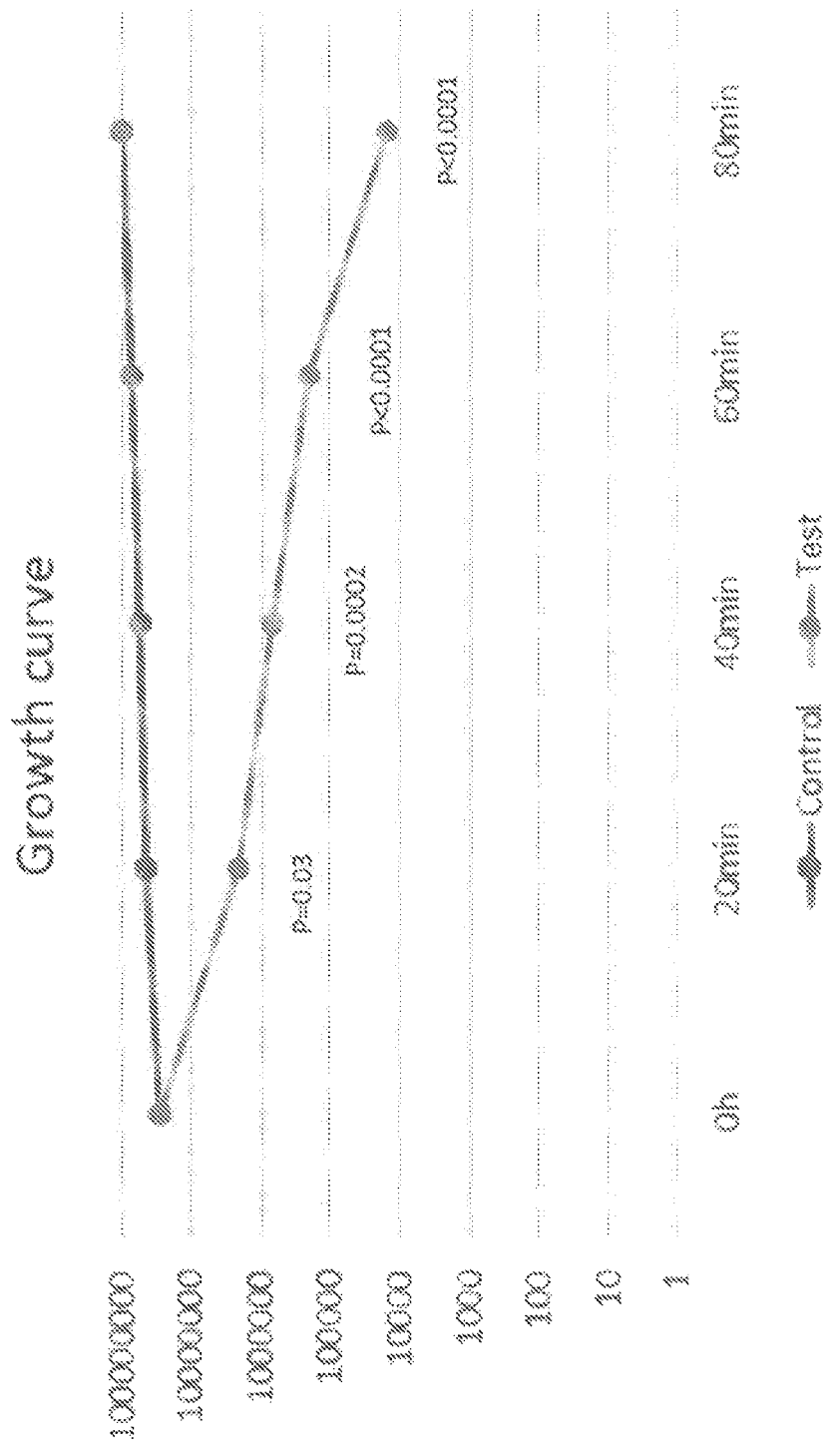
FIG. 12 illustrates an experimental data showing an example of a UV emitting device of the present disclosure being used to prevent of *E. coli* from proliferating.
Figure 13:
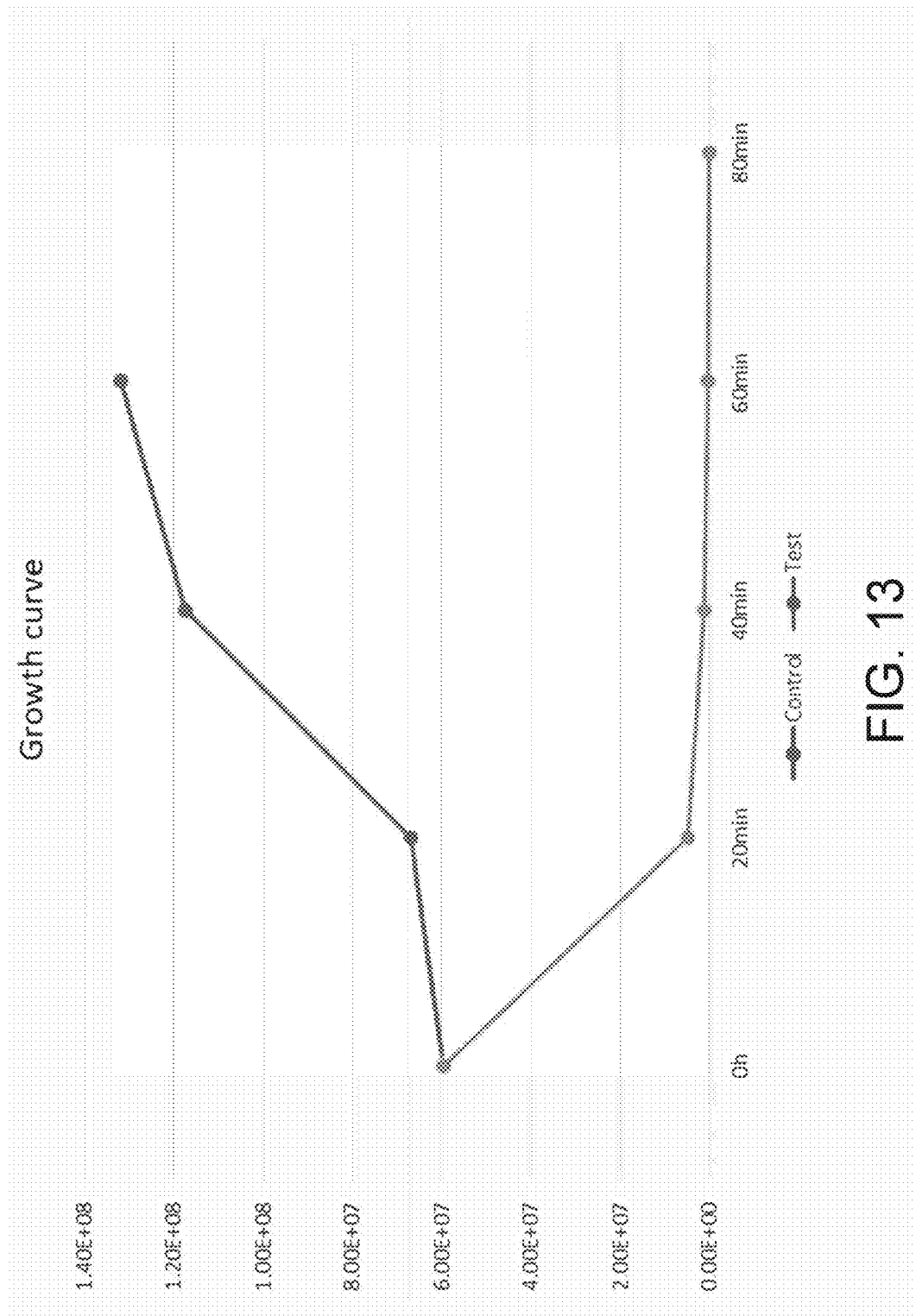
FIG. 13 illustrates another experimental data showing an example of a UV emitting device of the present disclosure being used to prevent of *E. coli* from proliferating.

FIGS. 12 and 13 illustrate an experimental data showing an example of a UV emitting device of the present disclosure being used to prevent of E. coli from proliferating. As shown, the control group where the UV light was not applied continued to grow, whereas the test group that had UV light applied through the UV emitting device showed continuous decrease in E. coli over time. The UV light is shown to both prevent E. coli from proliferating and also kill the bacteria over time.

Figure 16A:
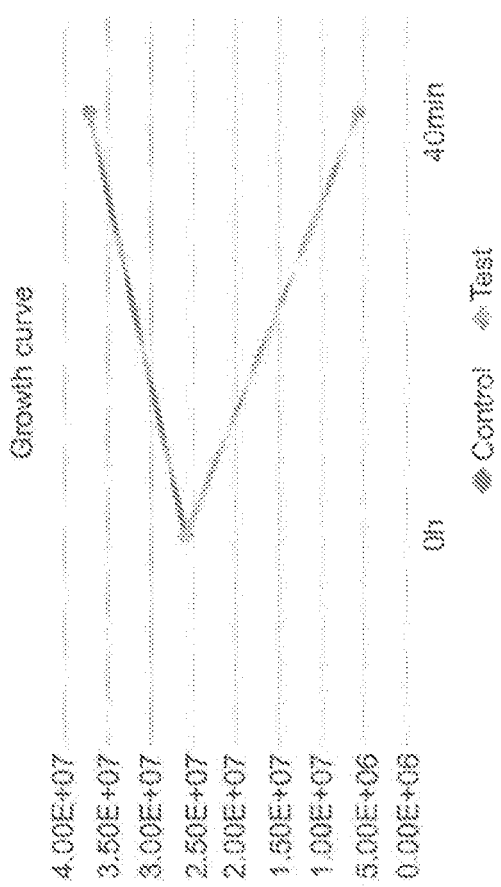
FIG. 16A illustrates an experimental data showing a use of an example of a UV emitting device of the present disclosure on a liquid culture containing *E. coli*.
Figure 16B:
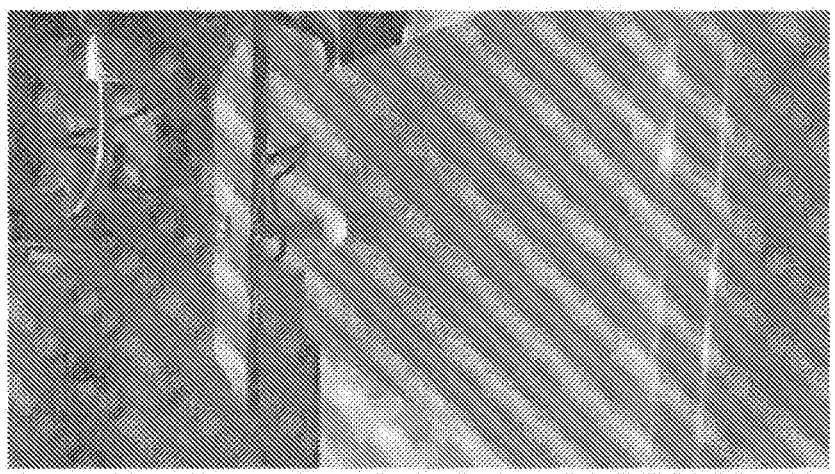
FIG. 16B illustrates an example of a UV emitting device of the present disclosure being used on a liquid culture containing *E. coli*.

FIG. 16B illustrates an example of a UV emitting device of the present disclosure being used on a liquid culture containing E. coli. The results of the experiment are shown in, e.g., FIGS. 16A, and 17-22. All of the results illustrate a significant reduction in the growth of E. coli in liquid samples where UV-A and UV-B lights were emitted by the UV emitting device of the present disclosure onto the liquid samples.

FIG. 16A illustrates results of an experiment carried out in accordance with conditions as shown in Table 1 below.

TABLE 1

| Results | | | | | | | | | | |
|---|---|---|---|---|---|---|---|---|---|---|
| 3/23/2017 | Intensity UVA: | 13 W/m2 | sides | | | | | | | |
| Liquid culture | Intensity UVC: | n/s | | | | | | | | |
| 2 ml tubes | Time of exposure: | 2400 seconds | | | | | | | | |
| blocked tip | Cumulative dose: | 31.2 KJ/m$^2$ | sides | | | | | | | |
| | | | 0 h | | | Median | | 40 min | | Median |
| | Control | 2.04E+07 | 2.41E+07 | 2.59E+07 | 2.41E+07 | 3.87E+07 | 3.57E+07 | | | 3.72E+07 |
| | Test | 2.04E+07 | 2.41E+07 | 2.59E+07 | 2.41E+07 | 6.00E+06 | 4.50E+06 | 6.06E+06 | 5.31E+06 | 5.66E+06 |
| | | 0 h | | 40 min | | | | | | |
| | Control | 2.59E+07 | | 3.72E+07 | | | | | | |
| | Test | 2.59E+07 | | 5.66E+06 | | | | | | |

Figure 17:
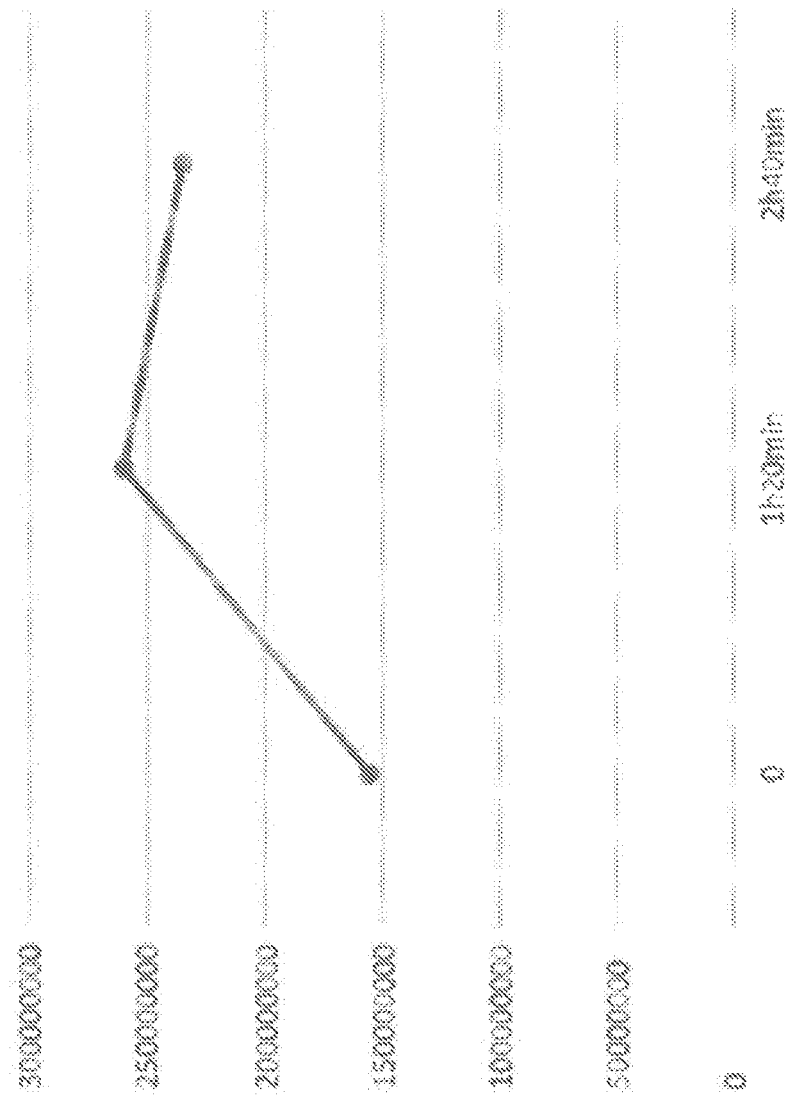
FIG. 17 illustrates an experimental data showing a use of an example of a UV emitting device of the present disclosure on a liquid culture containing *E. coli*.

FIG. 17 illustrates results of an experiment carried out in accordance with conditions as shown in Table 2 below.

TABLE 2

| Results | | | | | | |
|---|---|---|---|---|---|---|
| 2/20/2017 | | | | | Cumulative dose | |
| Liquid culture - big tube (5 ml) | | | | | UVA = 6 mW/cm | UVC = 10 uW/cm2 |
| | 0 | 1 h 20 min | 2 h 40 min | 1 h 20 min | 288 KJ/m2 | 480 J/m2 |
| test | 1.55E+08 | 2.60E+08 | 2.35E+08 | 2 h 40 min | 576 KJ/m2 | 860 J/m2 |

Figures 18A, 18B:
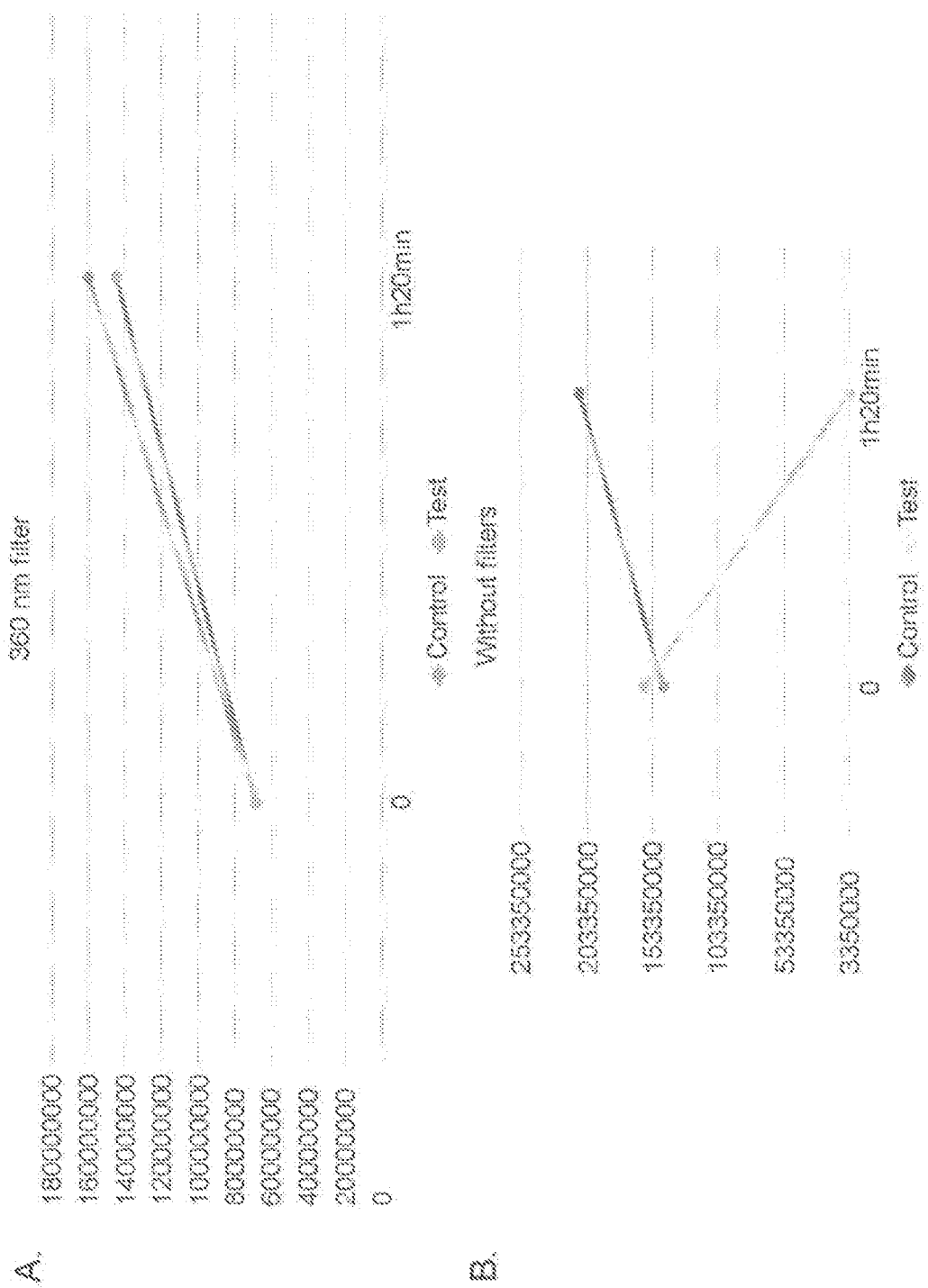
FIGS. 18A and 18B illustrate an experimental data showing a use of an example of a UV emitting device of the present disclosure on a liquid culture containing *E. coli*.

FIG. 18A illustrates results of an experiment carried out in accordance with conditions as shown in Table 3 below.

TABLE 3

| Results | | |
|---|---|---|
| Feb. 22, 2017 | | |
| Liquid culture-2 ml tube | | |
| | UVA = 6 mW/cm2 | UVC = 10 uW/cm2 |
| Cumulative dose | 288 KJ/m2 | 480 J/m2 |
| Sides | UVA = 80 uW/cm2 | |
| Cumulative dose | 3.8 KJ/m2 | |
| | Filter 360 mm | |
| | 0 | 1 h 20 min |
| Control | 6.85E+07 | 1.45E+08 |
| Test | 6.85E+07 | 1.60E+08 |

FIG. 18B illustrates results of an experiment carried out in accordance with conditions as shown in Table 4 below.

TABLE 4

| Results | | |
|---|---|---|
| Liquid culture-2 ml tube | | |
| | UVA = 18 mW/cm2 | UVC = 180 uM/cm2 |
| | 864 KJ/m2 | 8640 J/m2 |
| | UVA = 220 uW/cm2 | |
| | 10.56 KJ/m2 | |
| | Without filter | |
| | 0 | 1 h 20 min |
| Control | 1.45E+08 | 2.09E+08 |
| Test | 1.60E+08 | 3.35E+06 |

Figure 19:
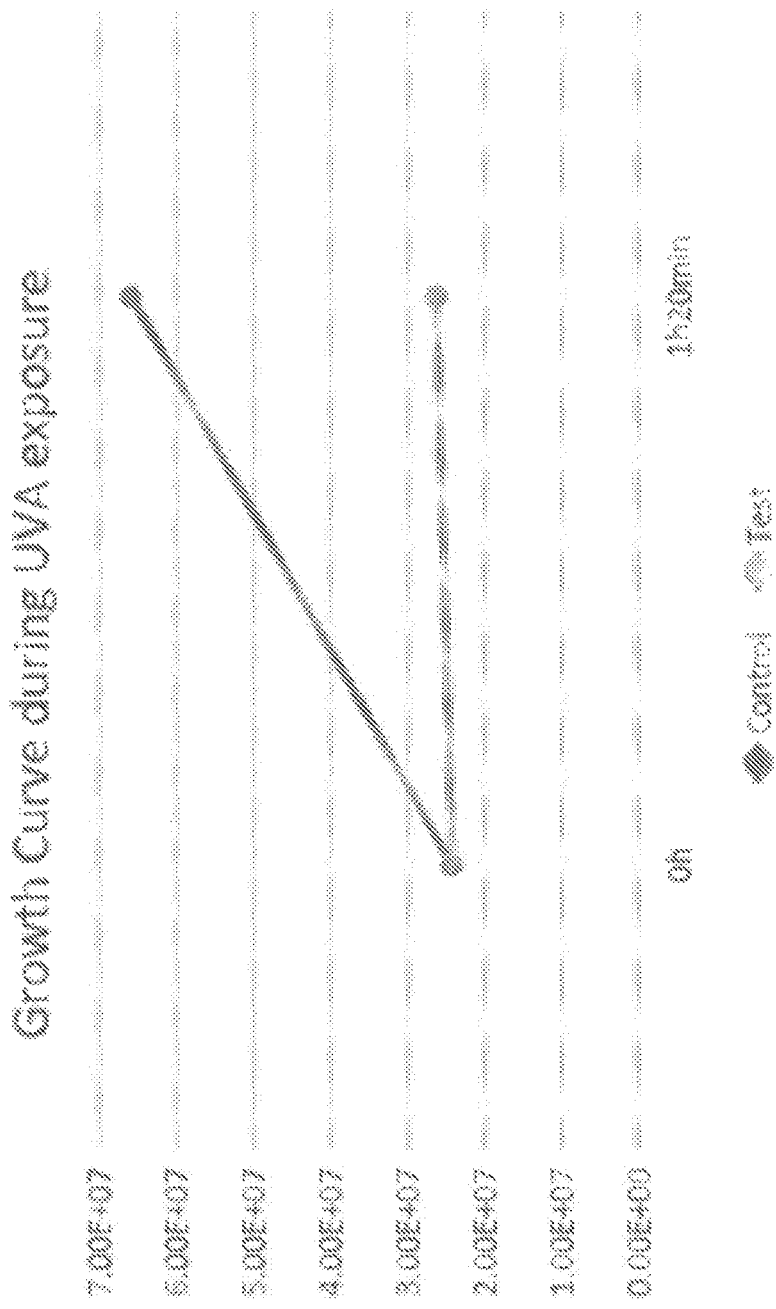
FIG. 19 illustrates an experimental data showing a use of an example of a UV emitting device of the present disclosure on a liquid culture containing *E. coli*.

FIG. 19 illustrates results of an experiment carried out in accordance with conditions as shown in Table 5 below.

TABLE 5

| Results | | | | |
|---|---|---|---|---|
| 2/28/2017 | | Intensity UVA: | 15 W/m2 tip | 1.98 W/m2 sides |
| Liquid culture - 2 ml tube | | Intensity UVC: | n/s | n/s |
| tip blocked | | Time of exposure: | 4800 seconds | |
| | | Cumulative dose: | 72 KJ/m2 tip | 9.5 KJ/m2 sides |
| | 0 h | 1 h 20 min | | |
| Control | 2.43E+07 | 6.59E+07 | | |
| Test | 2.43E+07 | 2.63E+07 | | |

Figure 20:
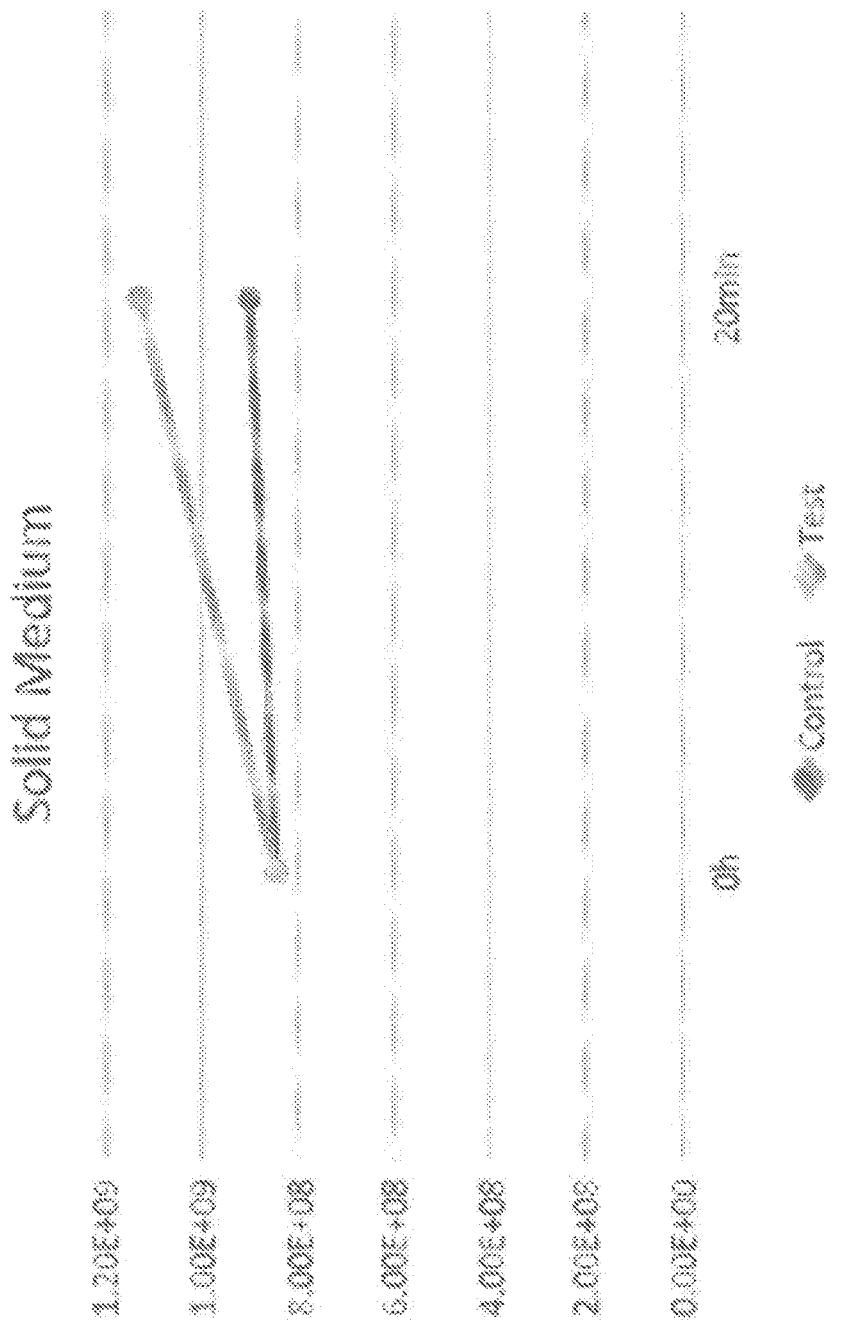
FIG. 20 illustrates an experimental data showing a use of an example of a UV emitting device of the present disclosure on a liquid culture containing *E. coli*.

FIG. 20 illustrates results of an experiment carried out in accordance with conditions as shown in Table 6 below.

TABLE 6

| Results | | | | |
|---|---|---|---|---|
| Mar. 9, 2017 | | Intensity UVA: | 13 W/m2 sides | |
| Liquid culture | | Intensity UVC: | n/s | |
| 2 ml tubes | | Time of exposure: | 1200 seconds | |
| tip blocked | | Cumulative dose: | 15.6 KJ/m2 sides | |
| | 0 h | 20 min | | |
| Control | 8.45E+08 | 9.00E+08 | | |
| Test | 8.45E+08 | 1.13E+09 | | |

Figure 21:
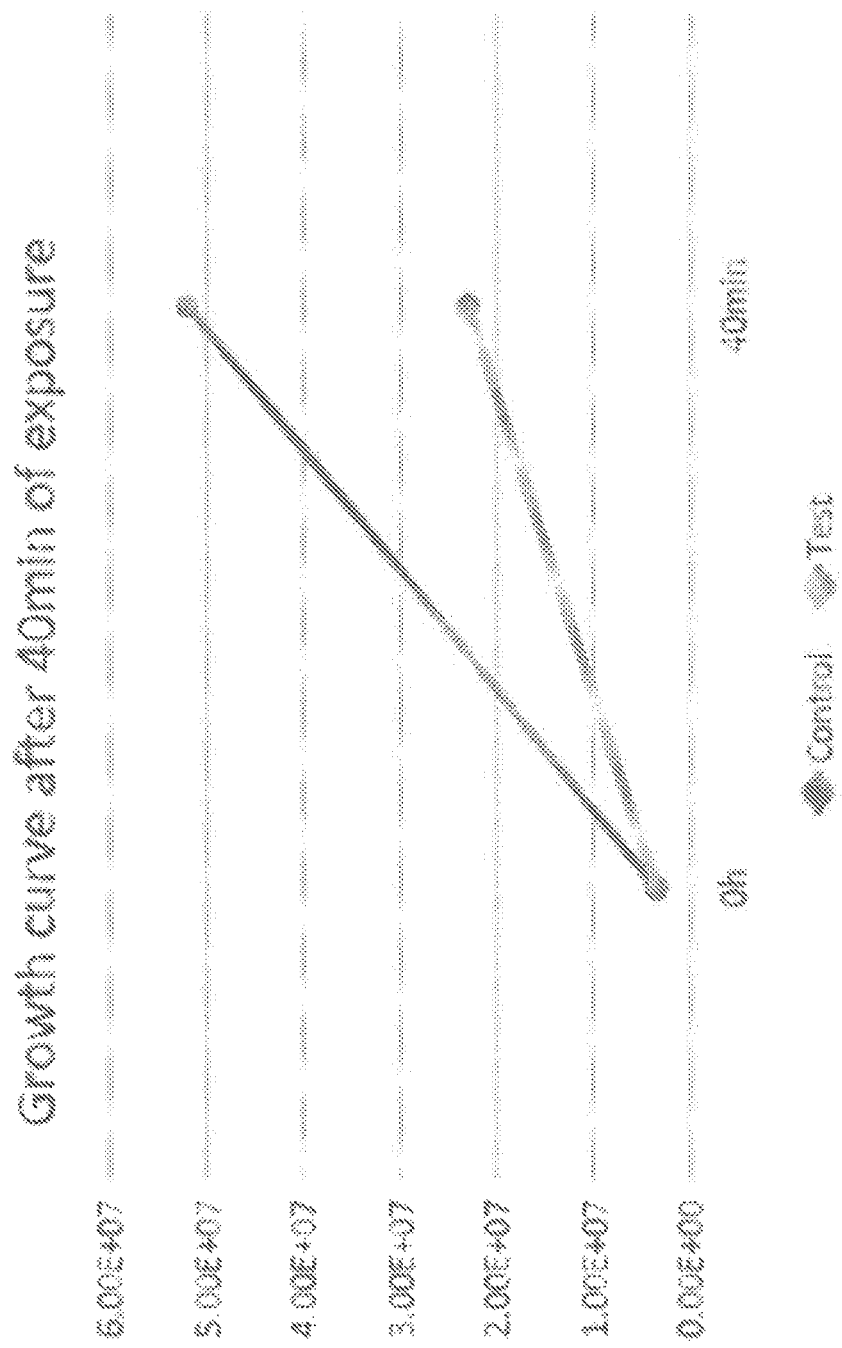
FIG. 21 illustrates an experimental data showing a use of an example of a UV emitting device of the present disclosure on a liquid culture containing *E. coli*.

FIG. 21 illustrates results of an experiment carried out in accordance with conditions as shown in Table 7 below.

TABLE 7

| Results | | | | |
|---|---|---|---|---|
| Mar. 14, 2017 | | Intensity UVA: | 13 W/m2 sides | |
| wax paper | | Intensity UVC: | n/s | |
| tip blocked | | Time of exposure: | 2400 seconds | |
| | | Cumulative dose: | 31.2 KJ/m2 sides | |
| | 0 h | 40 min | | |
| Control | 3.50E+06 | 5.20E+07 | | |
| Test | 3.50E+06 | 2.30E+07 | | |

Figure 22:
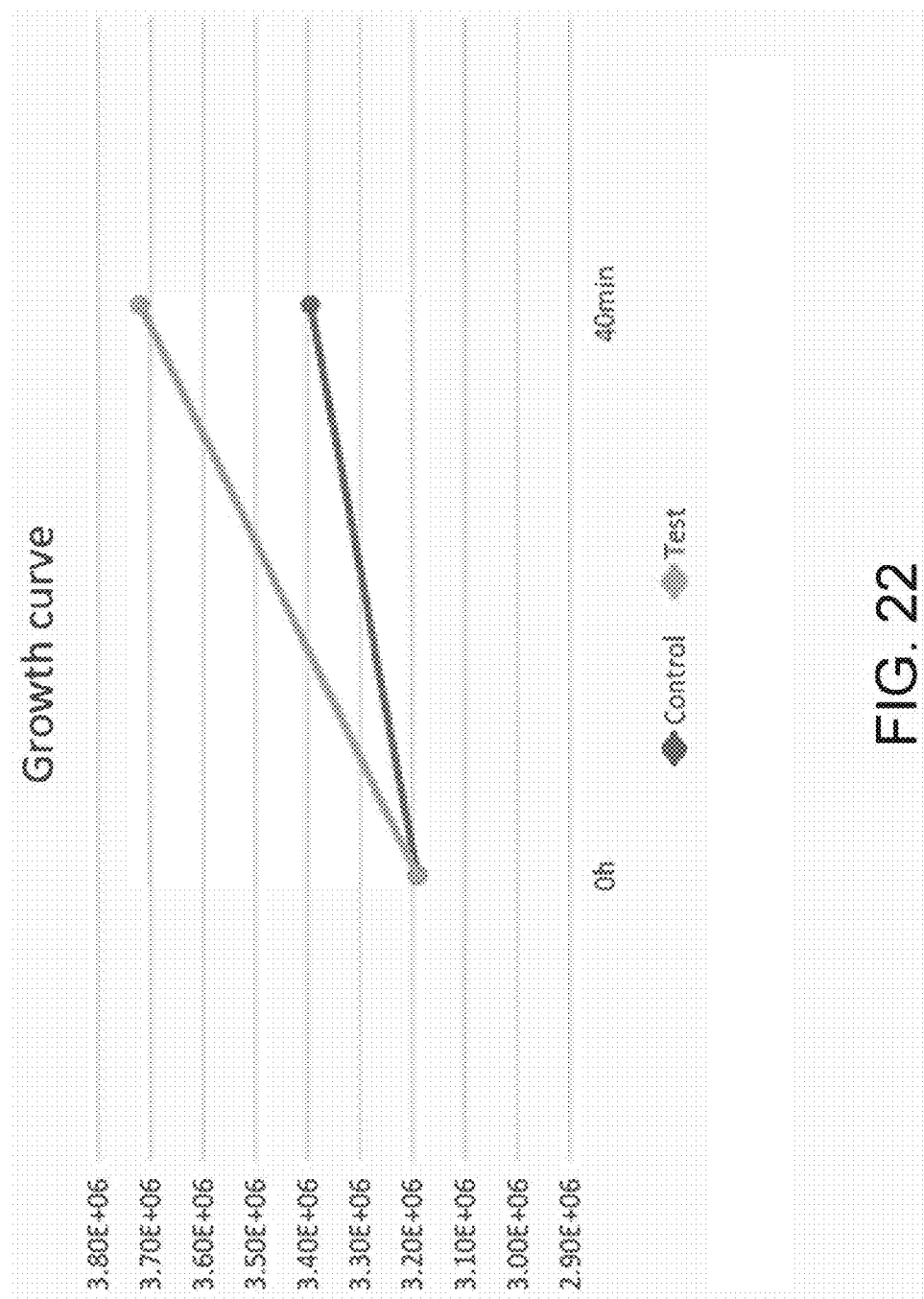
FIG. 22 illustrates an experimental data showing a use of an example of a UV emitting device of the present disclosure on a liquid culture containing *E. coli*.

FIG. 22 illustrates results of an experiment carried out in accordance with conditions as shown in Table 8 below.

TABLE 8

Results

3/20/2017 wax paper tip blocked
- Intensity UVA: 13 W/m2 sides
- Intensity UVC: n/s
- Time of exposure: 2400 seconds
- Cumulative dose: 31,2 KJ/m² sides

| | 0 h | | 40 min | | | 0 h | 40 min |
|---|---|---|---|---|---|---|---|
| Control | 3.88E+06 | 2.50E+06 | 4.06E+06 | 2.73E+06 | Control | 3.19E+06 | 3.40E+06 |
| Test | 3.88E+06 | 2.50E+06 | 4.07E+06 | 3.37E+06 | Test | 3.19E+06 | 3.72E+06 |

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and; or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A system for performing intra-corporeal ultraviolet therapy, the system comprising:
   a delivery tube,
      wherein the delivery tube is made from borosilicate,
      wherein the delivery tube includes at least an outer layer of transparent material to allow the emitted light to radiate out to internal cavities, and
      wherein the delivery tube is rigid;

at least one UV light source inside the delivery tube,
  wherein the at least one UV light source is configured to emit light at wavelengths in a UV-A range only, and
  wherein the at least one UV light source is positioned to deliver radiation directed outwardly around a circumference of the delivery tube; and
a power supply connected to the at least one UV light source.

2. The system of claim 1, wherein the at least one UV light source comprises a string of UV light sources that are distributed along the delivery tube, attached together with electrical connections, and connected to the power supply.

3. The system of claim 1, wherein the at least one UV light source is distributed along the entire portion of the delivery tube.

4. The system of claim 3, wherein the delivery tube is constructed such that the entire delivery tube glows and transmits UV light homogenously throughout the entirety of the delivery tube.

5. The system of claim 1, wherein the at least one UV light source is at least one LED.

6. The system of claim 1, wherein the at least one UV light source is a string of LEDs.

7. The system of claim 1, wherein emission of the light at wavelengths in the UV-A range only provides an intra-corporeal effect of damage to haploid DNA or RNA of microorganisms selected from the group consisting of bacteria, archaea, fungi, yeast, and viruses.

8. A method of treating a patient for an inflammatory or infectious condition inside the patient's body, the method comprising:
  providing the system of claim 1;
  inserting the delivery tube inside a patient cavity;
  turning on the power supply to emit light at wavelengths in a UV-A range only; and
  treating the patient for an inflammatory or infectious condition inside the patient's body.

9. The method of claim 8, wherein the patient cavity is a rectum, anus, mouth, or vagina.

10. A system for performing intra-corporeal ultraviolet therapy on a patient, the system comprising:
  a delivery tube adapted to be positioned inside an intra-corporeal cavity of a patient,
    wherein the delivery tube is made from borosilicate,
    wherein the delivery tube includes at least an outer layer of transparent material to allow the emitted light to radiate out to internal cavities,
    wherein the delivery tube is rigid, and
    wherein the intra-corporeal cavity is a rectum, anus, mouth, or vagina;
  at least one UV light source inside the delivery tube,
    wherein the at least one UV light source is configured to emit light at wavelengths in a UV-A range only, and
    wherein the at least one UV light source is positioned to deliver radiation directed outwardly around a circumference of the delivery tube; and
  a power supply connected to the at least one UV light source.

11. The system of claim 10, wherein the at least one UV light source comprises a string of UV light sources that are distributed along the delivery tube, attached together with electrical connections, and connected to the power supply.

12. The system of claim 10, wherein the at least one UV light source is distributed along the entire portion of the delivery tube.

13. The system of claim 12, wherein the delivery tube is constructed such that the entire delivery tube glows and transmits UV light homogenously throughout the entirety of the delivery tube.

14. The system of claim 10, wherein the at least one UV light source is at least one LED.

15. The system of claim 10, wherein the at least one UV light source is a string of LEDs.

16. The system of claim 10, wherein the light at wavelengths in the UV-A range only is effective for treatment of an infectious condition in the intra-corporeal cavity of the patient.

17. The system of claim 10, wherein the light at wavelengths in the UV-A range only is effective for treatment of an inflammatory condition in the intra-corporeal cavity of the patient.

18. The system of claim 10, wherein emission of the light at wavelengths in the UV-A range only provides an intra-corporeal effect of damage to haploid DNA or RNA of microorganisms selected from the group consisting of bacteria, archaea, fungi, yeast, and viruses.

* * * * *